(12) United States Patent
Farhadi

(10) Patent No.: US 6,592,530 B1
(45) Date of Patent: Jul. 15, 2003

(54) AUTOMATED HOT BIOPSY NEEDLE AND DEVICE

(75) Inventor: Ashkan Farhadi, 300 S. Maple Ave., Apt # D5, Oak Park, IL (US) 60302

(73) Assignee: Ashkan Farhadi, Oak Park, IL (US)

( * ) Notice: Subject to any disclaimer, the term of this patent is extended or adjusted under 35 U.S.C. 154(b) by 269 days.

(21) Appl. No.: 09/715,155

(22) Filed: Nov. 20, 2000

(51) Int. Cl.[7] .............................................. A61B 10/00
(52) U.S. Cl. ...................... 600/564; 600/568; 600/567; 606/167
(58) Field of Search ............................. 600/564–568; 606/167, 170

(56) References Cited

U.S. PATENT DOCUMENTS

| 4,953,558 A | * | 9/1990 | Akerfeldt | 600/564 |
| 5,121,751 A | * | 6/1992 | Panalletta | 600/567 |
| 5,284,156 A | * | 2/1994 | Schramm et al. | 600/567 |
| 6,273,862 B1 | * | 8/2001 | Privitera et al. | 600/568 |
| 6,432,065 B1 | * | 8/2002 | Burdorff et al. | 600/566 |

* cited by examiner

Primary Examiner—Max F. Hindenburg
Assistant Examiner—Charles Marmor, II

(57) ABSTRACT

An assembly for taking a biopsy sample from a site within the body of a patient includes a housing that is positioned over the bedside table of a patient and contains a biopsy actuator assembly used to propel the needles. The biopsy actuator includes a base-frame receiving a cannula slide and a stylet slide, each slide containing a needle holder for propelling the needles with the aid of one spring each. An electrical magnet-triggering device is provided for releasing the stylet slide, which in turn is adapted during the final phase of its propulsion to release the cannula slide. The housing fits to a needle assembly including a flexible guide tube, a flexible cannula and a stylet. The assembly further includes an electrocautery element and a mechanism for adjusting the forward speed and the depth of invasion of the needles.

9 Claims, 16 Drawing Sheets

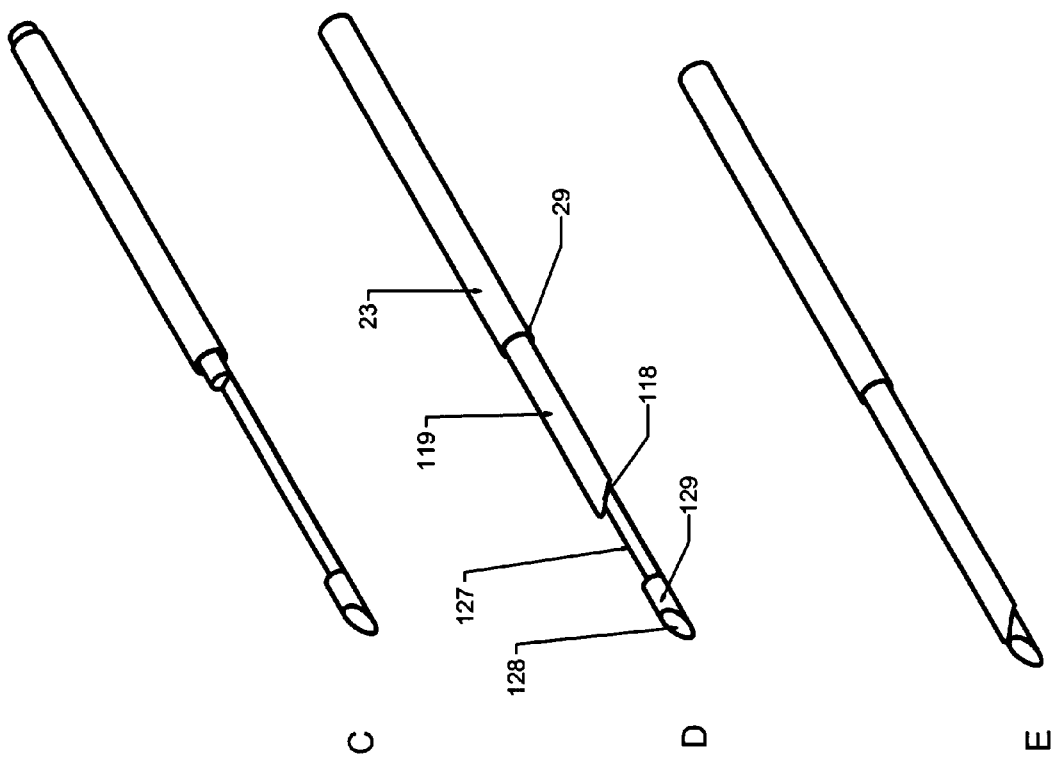
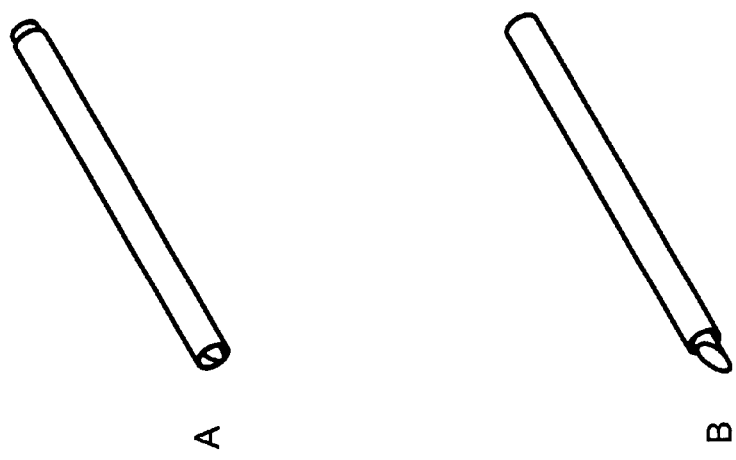
FIG. 16

AUTOMATED HOT BIOPSY NEEDLE AND DEVICE

FIELD OF INVENTION

This invention relates generally to a biopsy instrument; a device for removing a sample of tissue from a human being or an animal. More particularly, the invention relates to an automated biopsy instrument in which an outer cannula is driven over an inner stylet to obtain the tissue sample.

BACKGROUND OF INVENTION

The procedure known as biopsy, or the removal of samples of human and animal internal tissue, has been for many years a favored method for the nonsurgical diagnosis of tissue. Using biopsy needles one can take out samples from deeply located organs, such as the liver or the kidneys. This kind of sampling, is usually carried out in such a way that a doctor inserts a needle assembly through the skin and to the desired sampling location. Several kinds of biopsy needles are employed to biopsy the internal organs. One of the most commonly used needle assemblies comprises a slidably provided inner needle within a hollow outer needle. Using this kind of instrument, sampling has been performed in a two-step manual technique in which the outer hollow cutting cannula telescopically receives the inner stylet which is slidable between retracted and extended positions relative to the cannula. The sylet contains a specimen receiving slot near its sharpend distal end. In performing the first step of the technique, the physician places the tip of the needle (with the stylet retracted inside the cannula) against the tissue mass to be sampled and manually drives the stylet forward into the tissue mass. To carry out the second step, the physician manually drives the cutting cannula forwardly over the stylet, thereby severing a tissue sample and retaining it within the stylet slot inside the cannula's hollow interior. Then the entire needle assembly containing the collected tissue sample is withdrawn, whereafter the sample can be taken out and analyzed.

Examples of manually operated biopsy needles of this general type are disclosed in U.S. Pat. No. 4,700,014, issued Jul. 15, 1986 to D. Beraha for "Transrectal Prostate Biopsy Device and Method", and U.S. Pat. No. 3,477,423, issued Nov. 11, 1969 to L. K. Griffith for "Biopsy Instrument". Actually many physicians utilize a TRU-CUT® biopsy needle available from Travenol Laboratories, Inc. of Deerfield, Ill. that is described in above mentioned U.S. Pat. No. 3,477,423 to Griffith.

Such manually operated two-step devices are awkward to manipulate, and the tissue samples obtained may often be unsatisfactory. The depths to which the stylet and the cannula are driven into the tissue mass must be carefully controlled for accuracy and efficiency. Caution is required, as well, in applying the force with which the stylet and the cannula are plunged forward. Too little force may not sever the tissue sample from the mass. Too much force may cause unnecessary damage to the surrounding vital tissues.

Several automated biopsy instruments have been invented to improve the manual procedure and make it easier. The inventive idea resides in placing the needle assembly in a box, in which box there are provided propelling means for propelling the outer and/or inner needles, such that they carry out the above mentioned coordinated movements when the needle assembly has been located to the correct sampling position in the body. The needles are brought to carry out the desired movements in that the operator actuates a release mechanism outside of the box. The example of the automated devices are seen in U.S. Pat. No. 4,767,684, issued May 26, 1987 to H. G. Leigh for "Biopsy Device". It discloses a movable stylet telescopically received in a hollow movable cannula, both the stylet and the cannula being mounted to hubs within a pistol-style grip. In use the stylet is first manually advanced into the tissue and the cannula is then driven over the stylet by depressing a trigger.

A similar instrument designed by D. N. Mehl, through U.S. Pat. No. 4,733,671, issued Mar. 29, 1988, includes a pistol-style squeezable hand grip for single hand operation. A spring tensioned sliding cannula, including a configured cutting edge, actuates by a squeeze trigger and cam arrangement to slide over a fixed position stylet for entry into a tissue sample area.

Another automated device is found in U.S. Pat. No. 4,799,154, issued Oct. 13, 1987 to P. G. Lindgren for "Tissue Sampling Device". It is composed of a mechanism in which a release button is depressed to cause a spring-loaded stylet to be advanced into the tissue mass. The forward movement of the stylet also triggers the delayed release of a spring-loaded outer cannula, which slides over the stylet to sever the tissue sample.

U.S. Pat. No. 4,924,878, issued May 15, 1990 to J. E. Nottke for "Actuating mechanism for biopsy needle " and U.S. Pat. No. 4,958,625, issued Sep. 25, 1990 to J. S. Bates for "Biopsy needle instrument", disclose two other automated devices with sequential movement of the needles.

In any event, the various automated biopsy instruments presently known tend to be heavy and difficult to manipulate. Such limitations diminish the physician's control over the instrument and the precision with which biopsies may be performed. These instruments may be subject to inadvertent movement or torque which may, in turn, subject the patient to unnecessary trauma and risk.

Extensive bleeding can occur as a result of tissue resecting, which can lead to dangerous bleeding and complications. The idea of creating this device arrose after a complicated liver biopsy procedure. The patient developed exsanguinating blood loss through the peritoneum which led to an emergency laparatomy. This complication might be seen in tissue sampling of the visceral organ and is especially encountered in patients with bleeding diathesis. In an effort to remedy these problems, various techniques have been developed. For example, U.S. Pat. No. 3,598,108, issued Aug. 10, 1971 to K. Jamshidi for "Biopsy technique and biopsy device", discloses a biopsy technique and device involving the insertion of a biopsy needle into the tissue from which the specimen is to be taken, the needle having a sleeve member and the stylet therein, the stylet being removed and the biopsy being collected in the sleeve which is also thereafter removed. A heat transfer means such as a microcauter or a cryoprobe is inserted through the needle to project from the distal end thereof, which serves to cauterize the biopsy track as the needle and heat transfer means are removed as a unit.

In addition, U.S. Pat. No. 5,928,163, issued Jul. 27, 1999 to T. W. Roberts for "Biopsy sampler", discloses a "hot" biopsy procedure, using surgical forceps in which the jaws are electrodes (bipolar or monopolar). After the tissue sample is resected, the forceps are brought in contact with tissue remaining at the resecting site and RF energy is applied to the forceps to cause current to flow (i.e., cauterization) through the resecting site tissue to coagulate the tissue and stop the bleeding. Often, RF energy is applied to the forceps during resecting to help cut the tissue sample as well.

U.S. Pat. No. 5,810,806, issued Sep. 22, 1998 to M. A. Ritchart for "Methods and devices for collection of soft tissue", employs a combination of an electrosurgical cutting and a vacuum retrieving element, for sampling tissues.

U.S. Pat. No. 5,607,389, issued Mar. 4, 1997 to Edwards, et al. for "Medical probe with biopsy stylet" discloses several instruments for tissue collection. One of those embodiments includes a biopsy knife device in conjunction with an electromagnetic emitter for selective tissue sampling and electromagnetic heat ablation, or both.

U.S. Pat. No. 6,036,656, issued Mar. 14, 2000 to Slater, et al. for "jaw assembly having progressively larger teeth and endoscopic forceps instrument incorporating same" shows a design of an endoscopic forceps coupled to an electrocautery voltage supply for electrocoagulation of the biopsied tissue. Also U.S. Pat. No. 5,458,598, issued Oct. 17, 1995 to Feinberg for "cutting and coagulating forceps" discloses another type of forceps coupled with an electrocautery device for coagulating tissue after taking the biopsy sample.

All of these patents, incorporated herein by reference, and others, disclose typical prior art techniques and apparatus for gathering and removing a biopsy sample of tissue for further examination and review by a trained professional.

BRIEF SUMMARY OF THE INVENTION

The present invention is a further improvement in a biopsy sampling instrument, which is specially suited for viseral organ biopsies. Through the use of novel pneumatic controlling structure combined with electrocautery coagulation, the phsician can take out samples from deeply located organs easier and safer.

In one aspect, the invention features an assembly for taking a biopsy sample from a site within the body of a patient. The assembly includes a housing, which can be placed over a bed-side table and contains the biopsy needle actuator, a connection port and internal switches for appliance of an electrocautery device, a connection port and an external pedal switch for firing the actuator and a connection to the proximal end of a biopsy needle assembly. This housing not only provides the driving force for moving the stylet and the cannula forward in sequential manner, but also, it draws the needles back in to their initial (resting) position within the guide tube, after tissue sampling.

The needle apparatus includes a flexible probe that is composed of three components. A flexible plastic guide tube, which will be placed in the hand of the physician and can be guided to a point from which a sample is required. A moving cannula is telescoped within the guide tube and a notched sampling stylet is telescoped within the cannula. The tip of the stylet projects slightly from the distal end of the guide tube in percutaneous types of the needle to permit an easy penetration of intervening tissue by the sharpend tip of the sylet (e.g. subcutaneous tissue) prior to sampling. Indeed this penetration is not necessary in endoscopic type.

From another aspect, the employment of an electrocautery element in one preferred embodiment serves to cauterize the biopsy track before the needle is removed from the biopsied tissue after biopsy taking. Accordingly, the metal cannula and stylet are connected to a monopolar electrocautery device and the current is applied just after severing the tissue by forward movement of the cannula over the stylet in the tissue. Synchronizing the electrocautery appliance with the biopsy taking procedure produces electrocoagulation in the biopsy track before the needles are withdrawn. The electrical current applied to the surrounding tissue will not affect the sample tissue inside the hollow cannula due to good electrical and heat dissipation of the metal needles.

The advantages of the novel Automated Hot Biopsy Needle and Device over previous automated biopsy instruments include:

1. The housing of the majority of automated biopsy devices are grasped during the biopsy procedure. Therefore it is difficult to manipulate them especially in precise sampling. In this invention, the probe rather than housing would be grasped and manipulated by the physician, accordingly it would be easier for a physician to handle and manipulate a flexible probe especially in those situations that require high precision.
2. The biopsy needle actuator is fired by a pedal switch. This not only decreases the inadvertent movement of the needle location during biopsy taking, but also allows the physician to hold the probe with one hand while the other hand could be used to guide the probe for better localization (e.g. prostate biopsy) or to hold other instruments (e.g. laparascope or endoscope).
3. The present invention also includes a safety mechanism for preventing the accidental firing of the biopsy actuator. The safety mechanism includes an electronic timer based electrical switch on the front panel of the housing. Triggering of the biopsy actuator by firing buttons is only permitted during 20 seconds after pushing of the releasing activator button on the front panel of the housing. This period is also announced by a beeper.
4. In automated biopsy needle instruments, manual or spring loaded forward movement of the stylet into the tissue is followed sequentially by the release of spring loaded cannula for core sampling. In these devices the speed of sequential movement of the stylet and the cannula are fixed and relate to the spring force and the structural design of the instrument. The speed of forward movement of the stylet and the cannula can be adjusted in this device according to the tissue consistency. For example the speed of movement could be decreased in soft organs with low elasticity (e.g. liver) to decrease unnecessary damage to the surrounding tissue or inceased in more compact or elastic tissue to decrease the chance of unsatisfactory sampling.
5. The depth of biopsy can not be accurately predetermined by the majority of automated biopsy devices. In this technique and device the distance of the invasion of the biopsy needles from surface can be precisely predetermined.
6. This biopsy assembly can be used with conventional rigid or flexible endoscopes (i.e. laparascope, pleuroscope or other endoscopic procedures that need deep tissue biopsies).
7. Coupling an electrocautery device with the sampling procedure decreases the chance of bleeding complication. This not only decreases the bleeding risk and blood loss in usual biopsy procedures, but also makes the device useful in special circumstances (biopsy in bleeding diathesis or highly vascular organs).

Through use of this technique and device, biopsy specimens may be obtained easier, safer and more precisely. It also permits the physician to perform biopsies in patients with high risk of bleeding (e.g. bleeding diathesis, liver cirrhosis) or of those organs that bleed profusely after sampling (e.g. Spleen).

BRIEF DESCRIPTION OF THE SEVERAL VIEWS OF THE DRAWING

FIG. 6A is a left side view of the cannula slide.

FIG. 6B is a top view of the cannula slide.

FIGS. 6C & 6D are two isometric views of the cannula slide.

FIG. 7A is a left side view of the stylet slide.

FIG. 7B is a top view of the stylet slide.

FIGS. 7C & 7D are two isometric views of the stylet slide.

FIG. 10A is an isometric view of the assembly composed of a hollow shaft disposed slidably within a bush that would be fixed to the right side wall of the housing.

Extending a cannula flexible shaft from the housing, it passes through said hollow shaft.

FIG. 10B is a left side view of said assembly.

FIG. 10C is a front side view of said assembly.

FIG. 10d is an underside view of said assembly.

Figure 11:
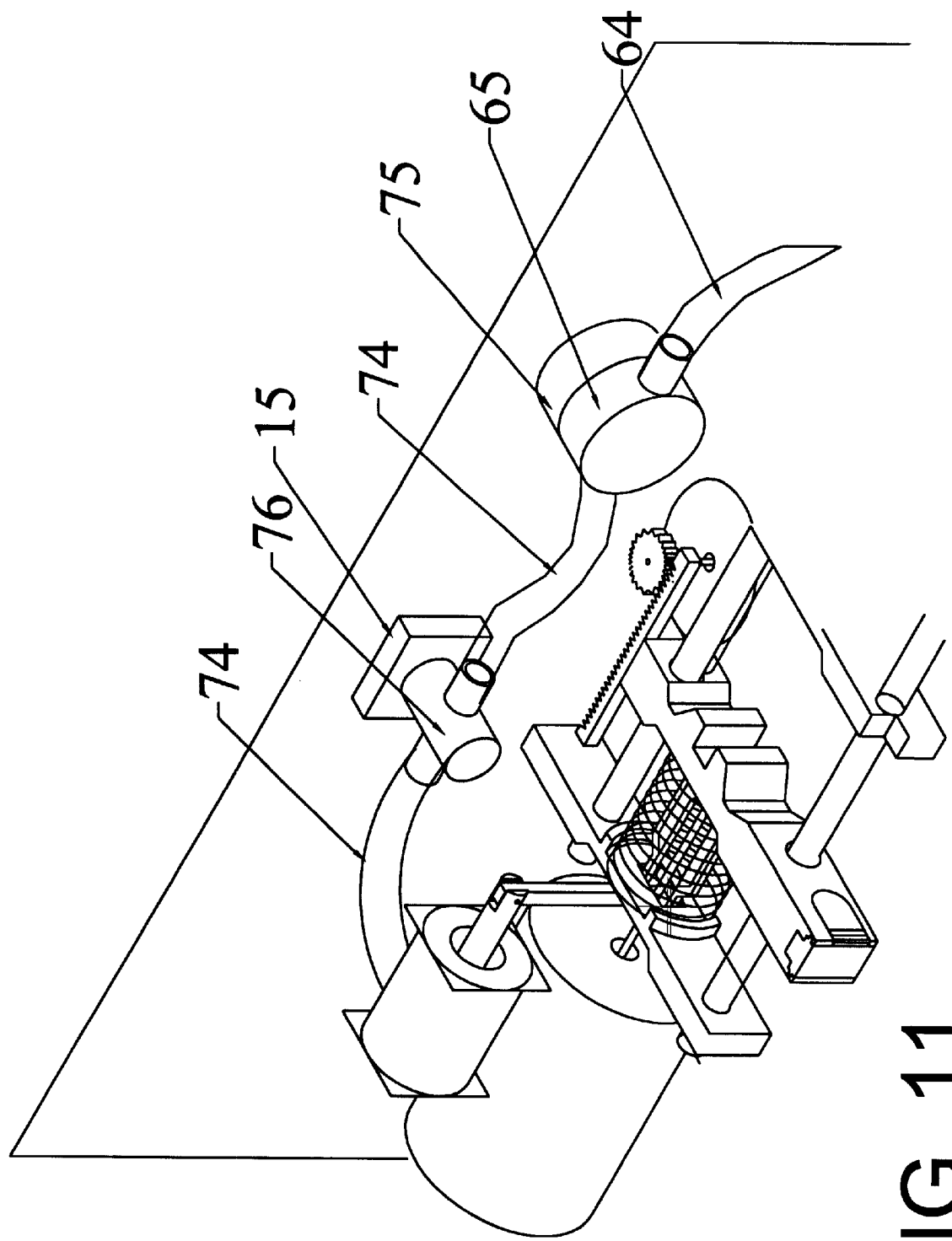

FIG. 11 Shows an isometric view of a portion of the biopsy actuator to show the details of the cannula slide forward speed control assembly and the mechanism for biopsy tissue retrieval after biopsy taking.

Figure 12:
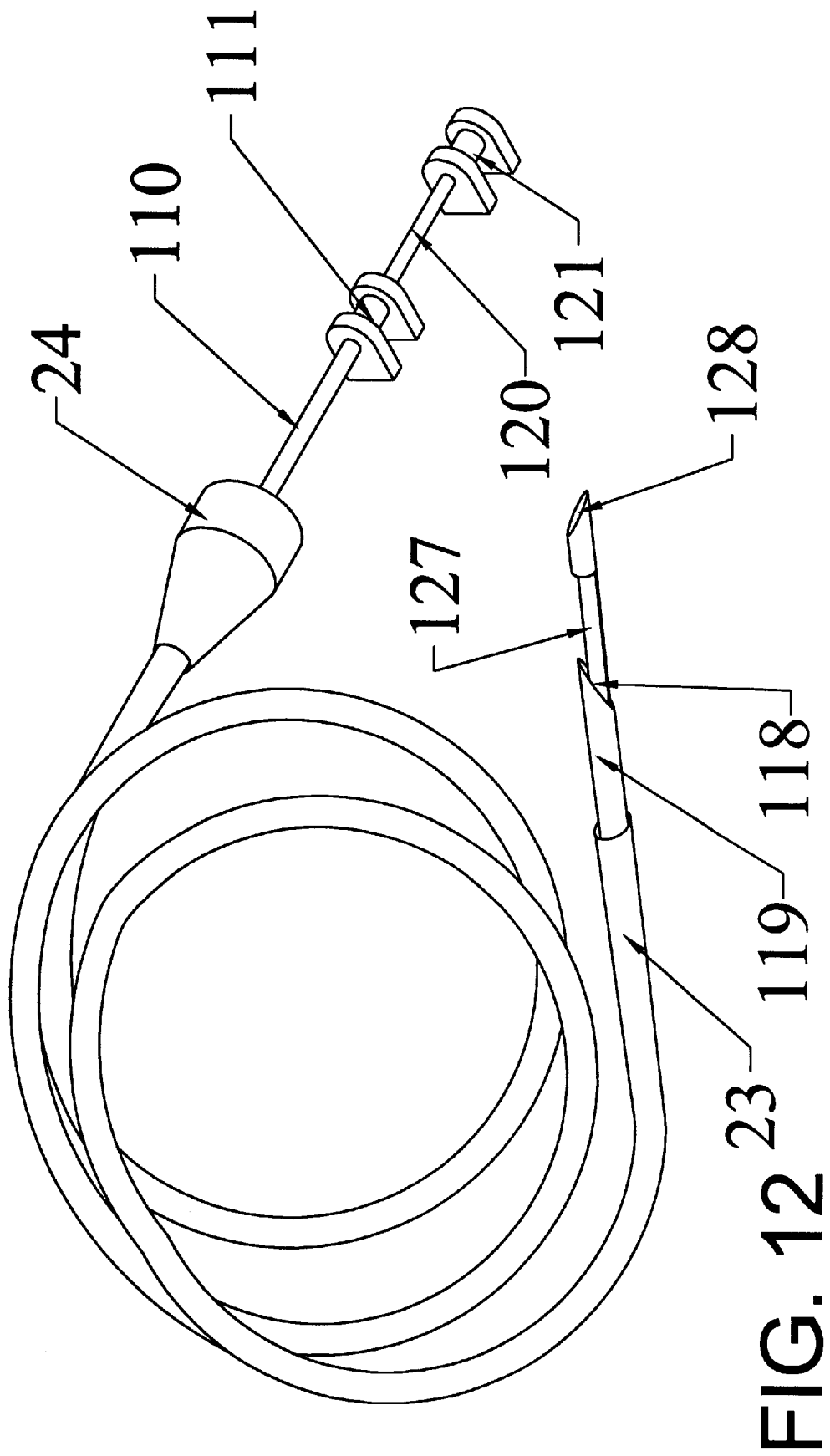

FIG. 12 shows an isometric view of the biopsy needle assembly, apart from the housing and biopsy actuator. It shows several components of the apparatus including the cannula needle tip, the cannula hub, the stylet needle tip, the stylet hub, guide tube and its nut.

Figure 13:
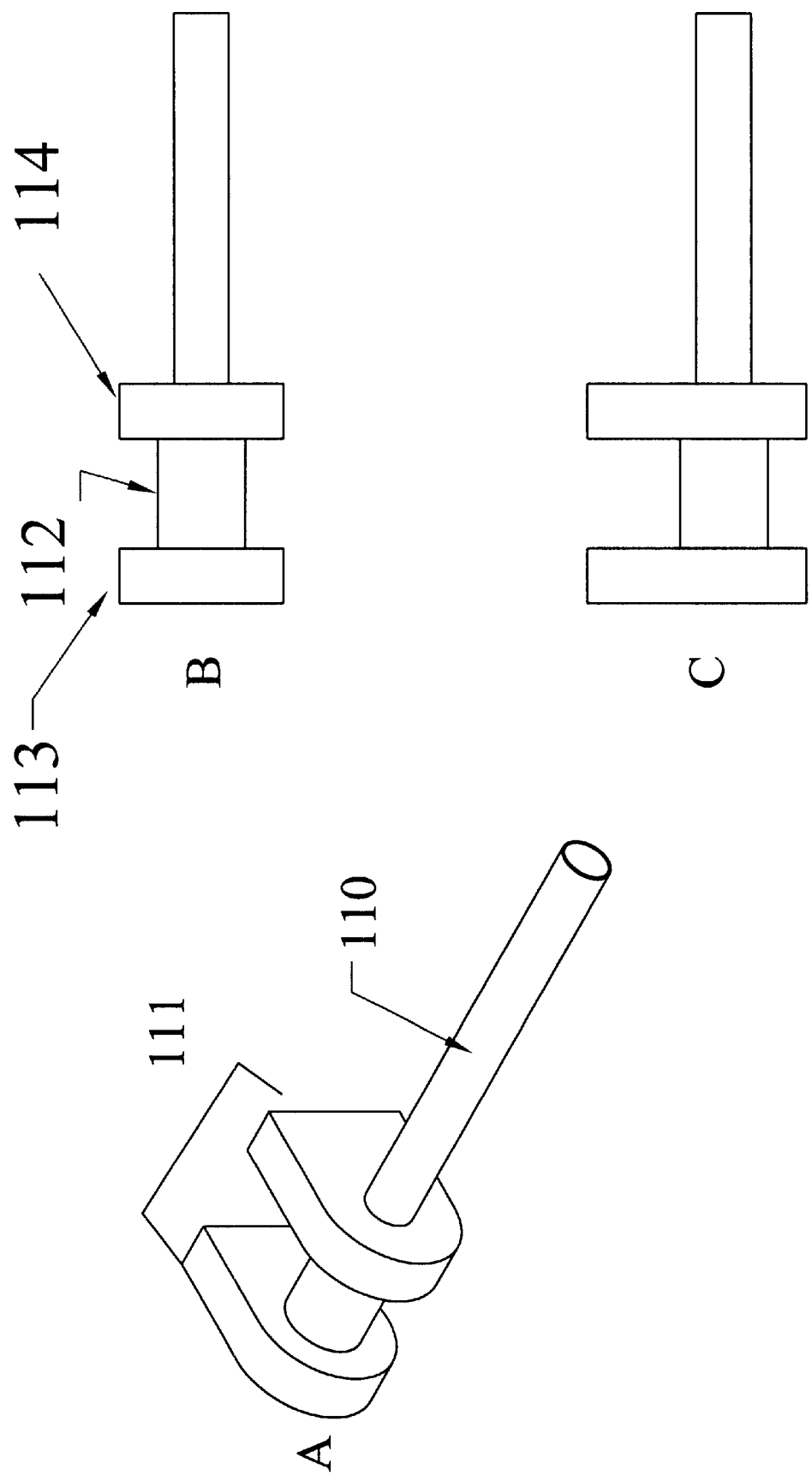

FIG. 13 shows several isometric and two-dimensional views of the cannula hub.

FIG. 13A is an isometric view of the cannula hub.

FIG. 13B is a front view of the cannula hub.

FIG. 13C is a top view of the cannula hub.

Figure 14:
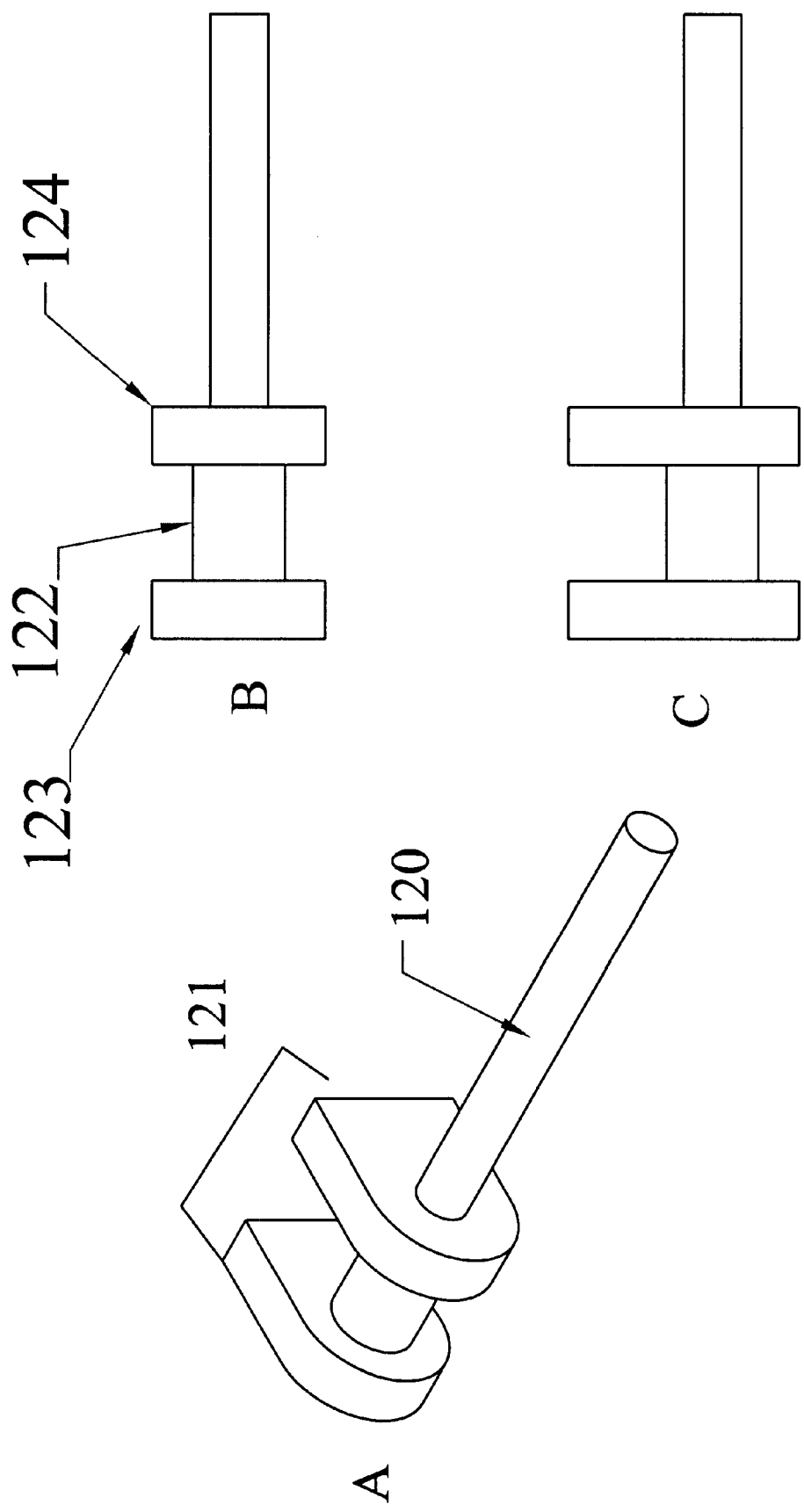

FIG. 14 shows several isometric and two-dimensional views of the stylet hub.

FIG. 14A is an isometric view of the stylet hub.

FIG. 14B is a front view of the stylet hub.

FIG. 14C is a top view of the stylet hub.

Figure 15:
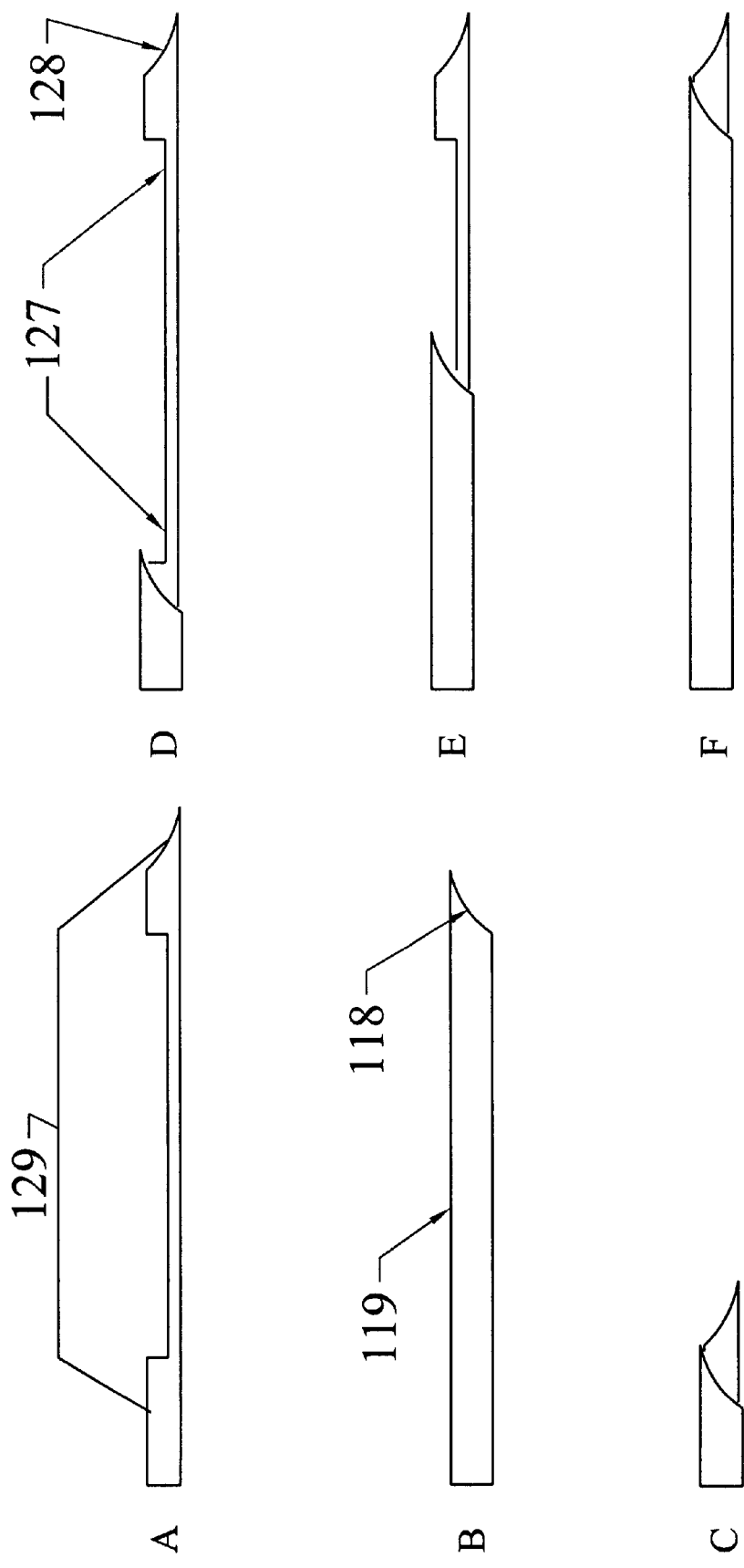

FIG. 15 shows several two-dimensional views of the tip of the biopsy needle assembly. It shows the tip of the cannula and the stylet needles in isolated form and during several stages of the biopsy procedure.

FIG. 15A is a side view of the tip of the stylet needle.

FIG. 15B is a side view of the tip of the cannula needle.

FIG. 15C is a side view of the tip of the needle assembly in resting phase before initiation of the biopsy procedure. The cannula needle covers the stylet needle and only the piercing tip of the stylet needle is exposed.

FIG. 15D is a side view of the tip of the needle assembly during the biopsy procedure. The stylet needle is protruded from the tip of the cannula needle.

FIG. 15E is a side view of the tip of the needle assembly during the biopsy procedure. The cannula needle is covering the protruded stylet needle. At this time the cutting tip of the cannula needle is severing the tissue sample from the patient's body and holding the severed sample in the tissue sampling notch of the stylet needle.

FIG. 15F is a side view of the tip of the needle assembly during the biopsy procedure. The cannula needle covers substantially completely the protruded stylet needle. By the time the cutting tip of the cannula needle reaches the end of its journey over the stylet needle, the severed tissue sample from the patient's body is held in the tissue sampling notch of the stylet needle.

FIG. 16 shows several isometric views of the tip of the needle assembly. It shows the tip of the guide tube, the cannula and the stylet needles in several stages of the biopsy procedure.

FIG. 16A is an isometric view of the tip of the needle assembly (endoscopic type) in resting phase before initiation of the biopsy procedure.

FIG. 16B is an isometric view of the tip of the needle assembly (percutaneous type) in resting phase before initiation of the biopsy procedure.

FIG. 16C is an isometric view of the tip of the needle assembly during the biopsy procedure. The stylet needle protruded from the tip of the cannula needle and guide tube.

FIG. 16D is an isometric view of the tip of the needle assembly during the biopsy procedure. The cannula needle is protruding from the tip of the guide tube covering the protruded stylet needle. At this time the cutting tip of the cannula needle is severing the tissue sample from the patient's body and holding the severed sample in the tissue sampling notch of the stylet needle.

FIG. 16E is an isometric view of the tip of the needle assembly during the biopsy procedure. The cannula needle is protruded from the tip of the guide tube to cover substantially the protruded stylet needle. By the time the cutting tip of the cannula needle reaches the end of its journey over the stylet needle, the severed tissue sample from the patient's body is held in the tissue sampling notch of the stylet needle.

DETAILED DESCRIPTION OF THE INVENTION

Figure 1:
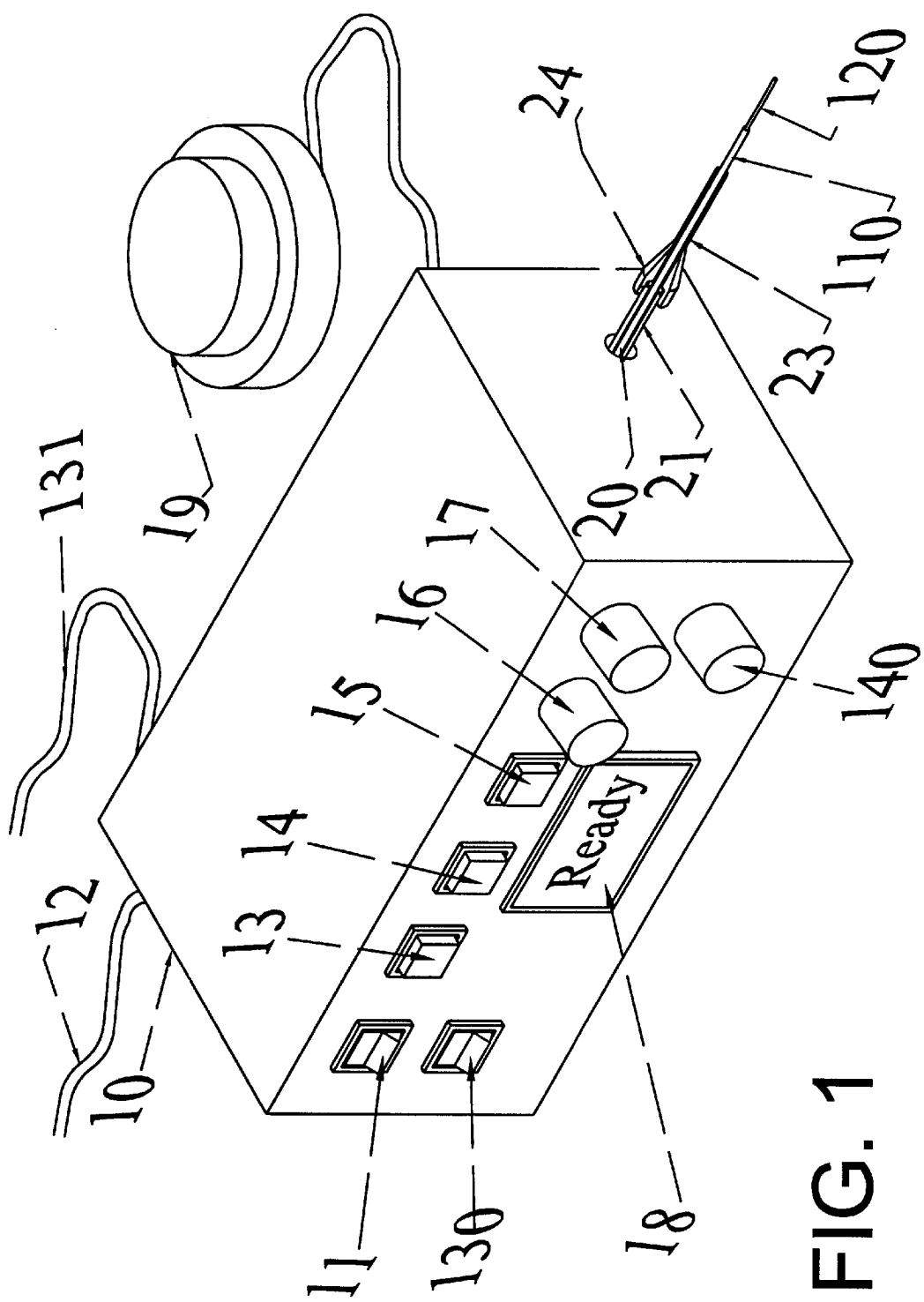
FIG. 1 is an isometric view of the housing of the biopsy actuator containing several buttons, control knobs and a digital display.

Automated Hot Biopsy Device is made up of several components:

A—Housing: As it is depicted in FIG. 1, the housing 10 is composed of a cubic box which contains several buttons and control knobs on its front panel. It can be placed over a patient's bed side table for easy access. The components include:

Main power switch 11 that turns the instrument on/off.

Electrocautery switch 130 that turns the electrocautery current on/off during biopsy procedure. Using this switch, it would be possible to perform biopsy procedure with or without electrocautery current coupling, respectively.

Releasing activator button 13. Pushing of this button permits the biopsy actuator to be triggered by firing button 14 or specimen retrieval button 15 within twenty seconds. This interval will be announced by a beeper which is positioned inside the housing. This button is part of the safety mechanism that prevents inadvertent firing of the biopsy needle by pedal firing button 19, firing button 14 or specimen retrieval button 15 on the front panel of the housing 10.

Firing button 14. Pushing of this button within 20 seconds of pushing of the releasing activator button 13 results in triggering of the biopsy actuator 30, which results in (sequential) movement of the stylet needle 129 and the cannula needle 119 to perform biopsy procedure. This button is equivalent to pedal firing button 19.

Specimen retrieval button 15. Pushing of this button within 20 seconds of pushing of the releasing activator button 13 results in slow protrusion of the stylet needle 129 for retreival of the specimen from the stylet tissue collecting slot 127. Releasing of this button results in returning of the stylet needle 129 to its primary position inside the cannula needle 119.

The stylet and cannula forward speed control knob 16 controls the forward movement speed of the stylet needle 129 and the cannula needle 119 inside the tissue during the biopsy procedure. Turning this knob will adjust the valves 75 & 65 that control the passage of outlet compressed air, from speed controlling cylinders.

Withdrawal lag time control knob 17. This control knob adjusts the lag time for appliance of the electrocautery current to the biopsy track that starts just after severing and collecting of the tissue specimen by the cannula needle 119 before withdrawal of the needles in to the guide tube. The duration of lag time together with the type and magnitude of the electrocautery current can determine the extent of the electrocoagulation.

Depth of needle invasion control knob 140. This control knob adjusts the depth of invasion of the stylet tip 128 and the cannula cutting tip 118 within the tissue. This is done by changing the position of the guide tube proportional to the cannula and the stylet needles 119 & 129. Moving guide tube 23 in proportion to the cannula flexible hollow shaft 110 and the stylet wire 120 results in more or less protrusion of the cannula needle 119 and the stylet needle 129 from the distal end of the guide tube 23.

Digital display 18 shows the necessary information about the device action and condition. It may show presence or absence of electrocautery coupling, readiness of biopsy actuator for firing, specimen retrieval, forward speed of the stylet needle 129 and the cannula needle 119 and withdrawal speed of the needles.

Pedal firing button 19 and its cable, which is connected through the back wall of the housing 10, is a counterpart of firing button 14. Pushing of this button by a physician's foot results in firing of the biopsy actuator 30 within permited interval (20 seconds) that started after pushing of the releasing activator button 13 on the housing 10.

An opening 20 through which, the cannula flexible hollow shaft 110 and the stylet wire 120 can extend from their needle hubs 111 & 121, is provided on the right wall of the housing 10. The stylet wire 120 and the cannula flexible hollow shaft 110 pass through a hollow shaft 21 that secure to the proximal end of the guide tube 23 via guide tube nut 24. The stylet wire 120 and the cannula flexible hollow shaft 110 are disposed within guide tube 23 and telescoping with respect thereto.

There are several cable connections to the housing 10. One of those connect housing to the pedal firing button 19. The other two cables connect housing 10 to the electricity power supply 12 and electrocautery device 131.

Figure 2:
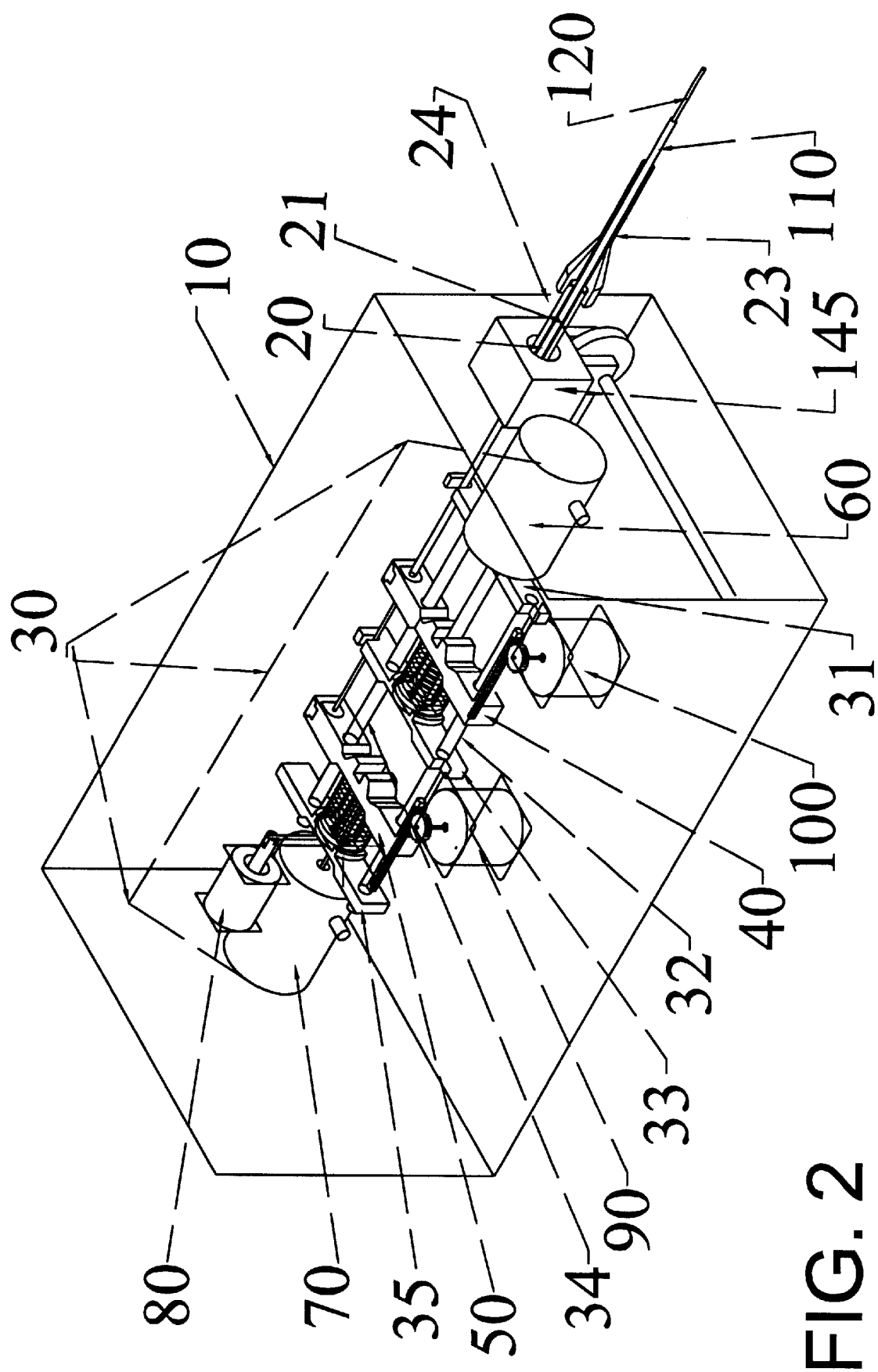
FIG. 2 is an isometric view of the biopsy actuator inside the housing.

B—Biposy acuator assembly: FIG. 2 is an isometric view of the housing where the biopsy actuator 30 is disposed. In this view the relation of the biopsy actuator 30 and the housing 10 is obvious. The biopsy actuator 30 is composed of several components.

The biopsy actuator base-frame is made up of 2 cylindrical solid shafts 32 & 34 that act as sliding guideways for movement of the cannula slide 40 and the stylet slide 50. These guideways are kept parallel with the support of three fixed jaws 31, 33, 35. The left 35, middle 33 and right 31 fixed jaws attach securely to the left, middle and right end of the guideway shafts respectively. The cannula slide 40 moves easily on the guideway shaft back and forth between the right and middle fixed jaws 31, 33. The stylet slide 50 moves easily on the guideway shafts back and forth between the middle and left fixed jaws 33, 35. The stylet speed control cylinder 70 and the cannula speed control cylinder 60 are seen on the left and right side of the biopsy actuator 30. The stylet and the cannula cocking electromotors 90, 100 are seen on the front left and right of the biopsy actuator 30 respectively.

Figure 3:
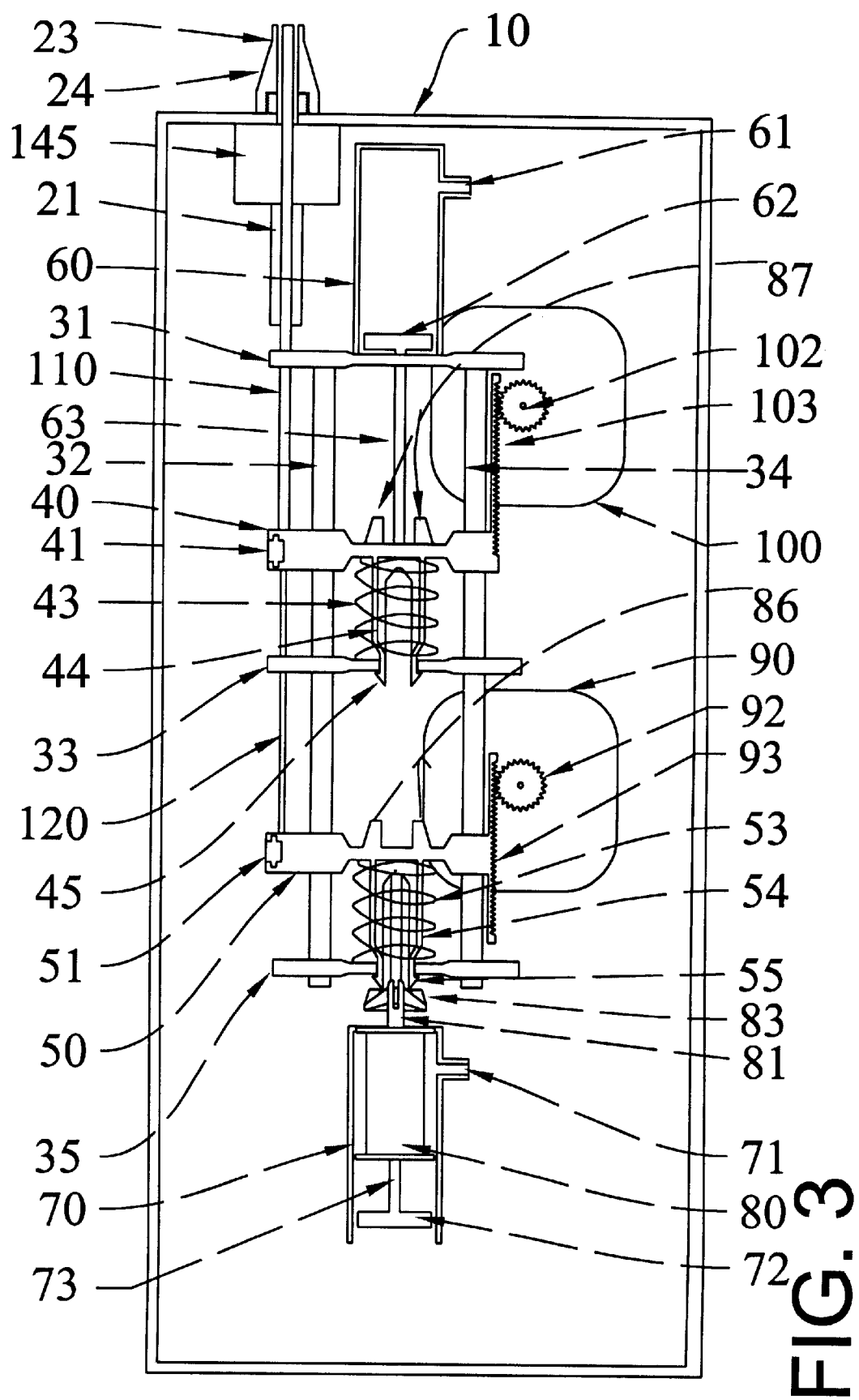
FIG. 3 is a cut-away of the biopsy actuator assembly inside the housing, viewed from top.

FIG. 3 is a cut-away of the biopsy actuator assembly veiwed from top. It shows the breach mechanism for firing the biopsy needle assembly to take a biopsy sample. The breach mechanism includes a cannula slide 40 for propelling the cannula needle 119 and a stylet slide 50 for propelling the stylet needle 129 during taking of a biopsy specimen.

Figure 4:
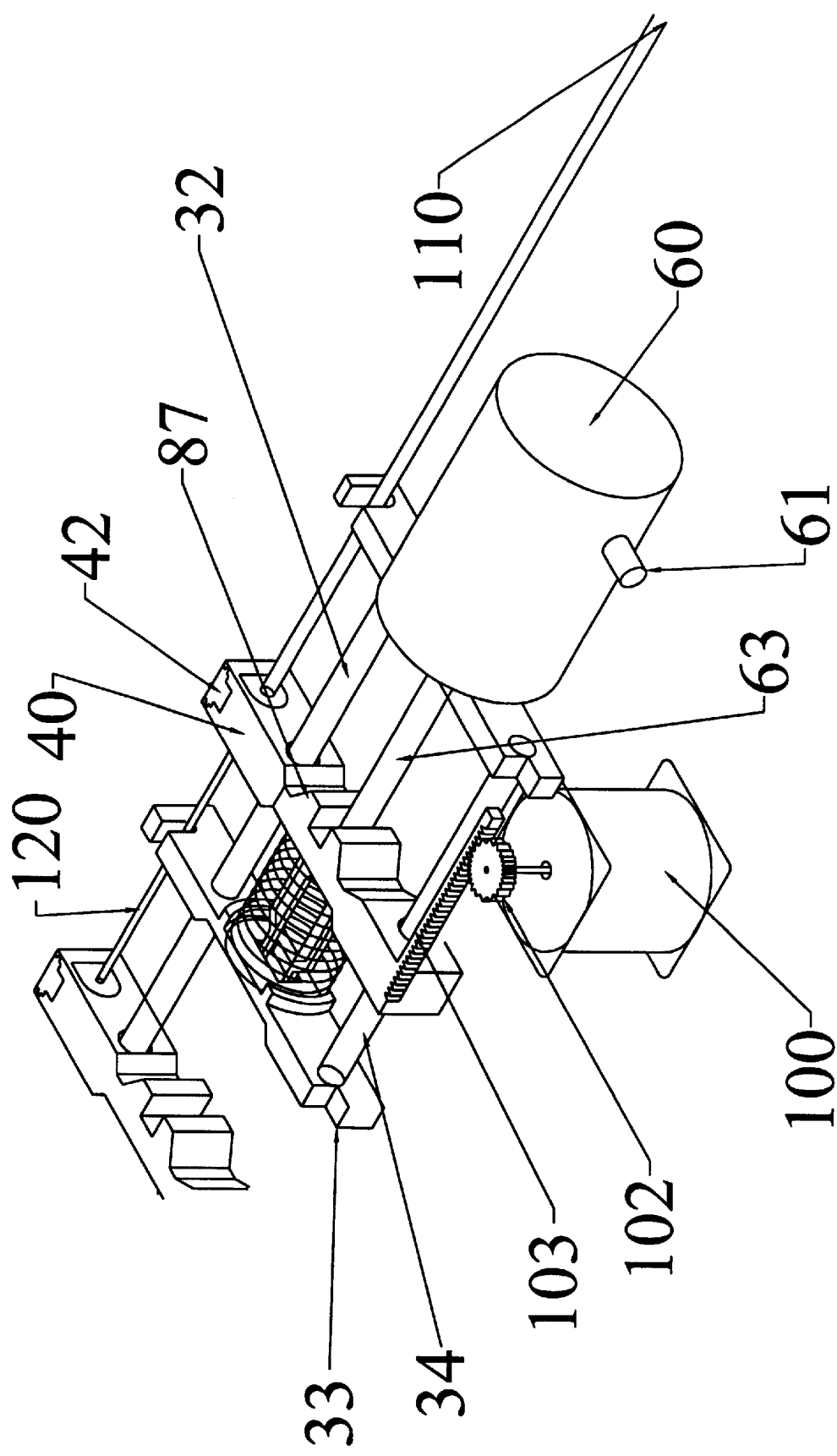
FIG. 4 is an isometric view of a portion of the biopsy actuator to show the details of the cannula slide and its related components.

FIG. 4 is a magnified portion of the biopsy actuator that shows more details of the cannula slide and its related components. As it is depicted in this isometric veiw, the cannula slide 40 is biased in a forward position by a helical spring 43. The cannula slide 40 has a recess area 41 and a cover 42 for receiving the needle hub 111 of the cannula and a pair of lumens 46,47 for receiving guide-way shafts 32,34.

Figure 5:
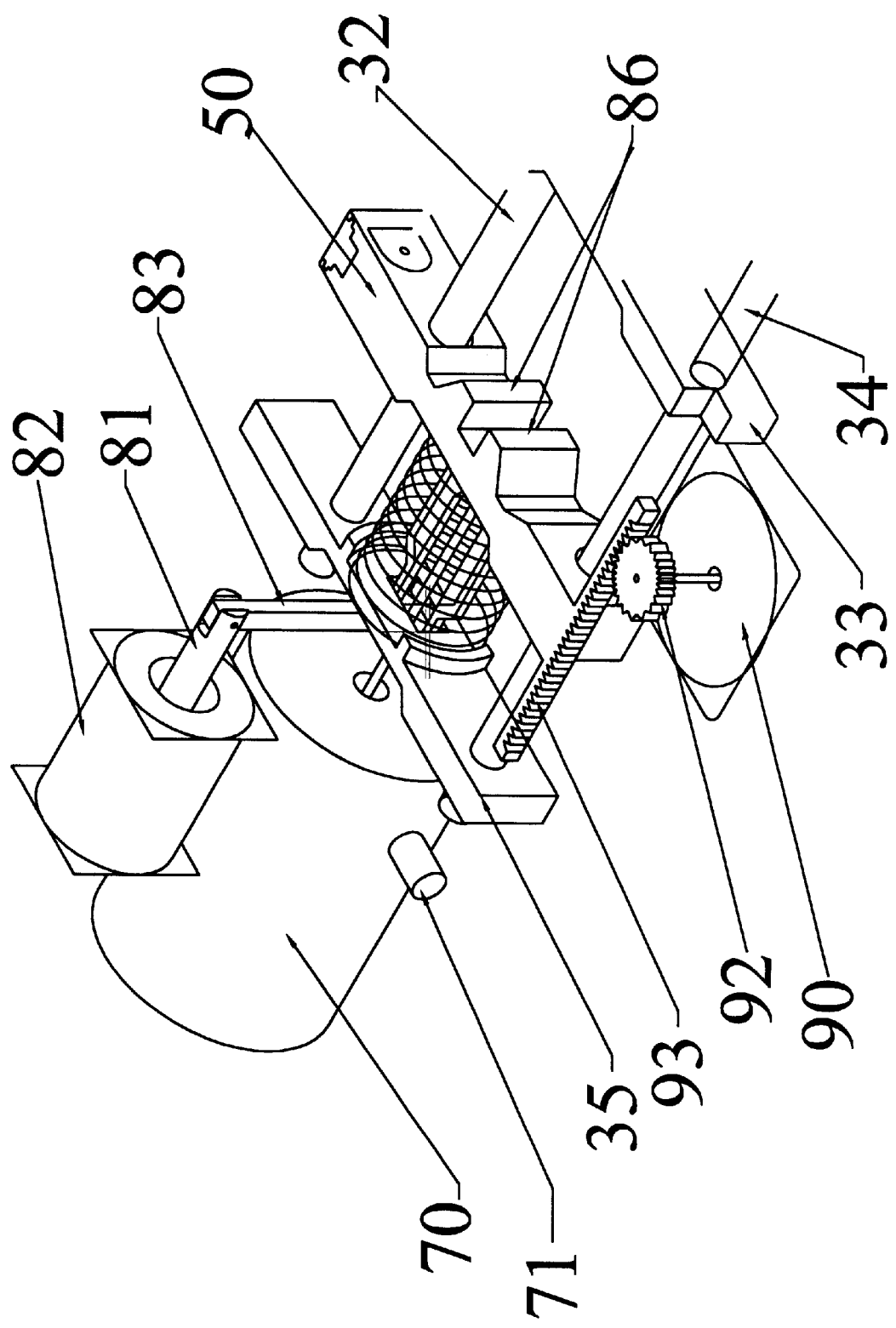
FIG. 5 is an isometric view of a portion of the biopsy actuator to show the details of the stylet slide and its related components.

FIG. 5 is a magnified portion of the biopsy actuator that shows more details of the stylet slide and its related components. As it is depicted in this isometric veiw, the stylet slide 50 is biased in a forward position by a helical spring 53. The stylet slide 50 has a recess area 51 and a cover 52 for receiving the needle hub 121 of the stylet and a pair of lumens 56,57 for receiving guide-way shafts 32,34.

Figure 6:
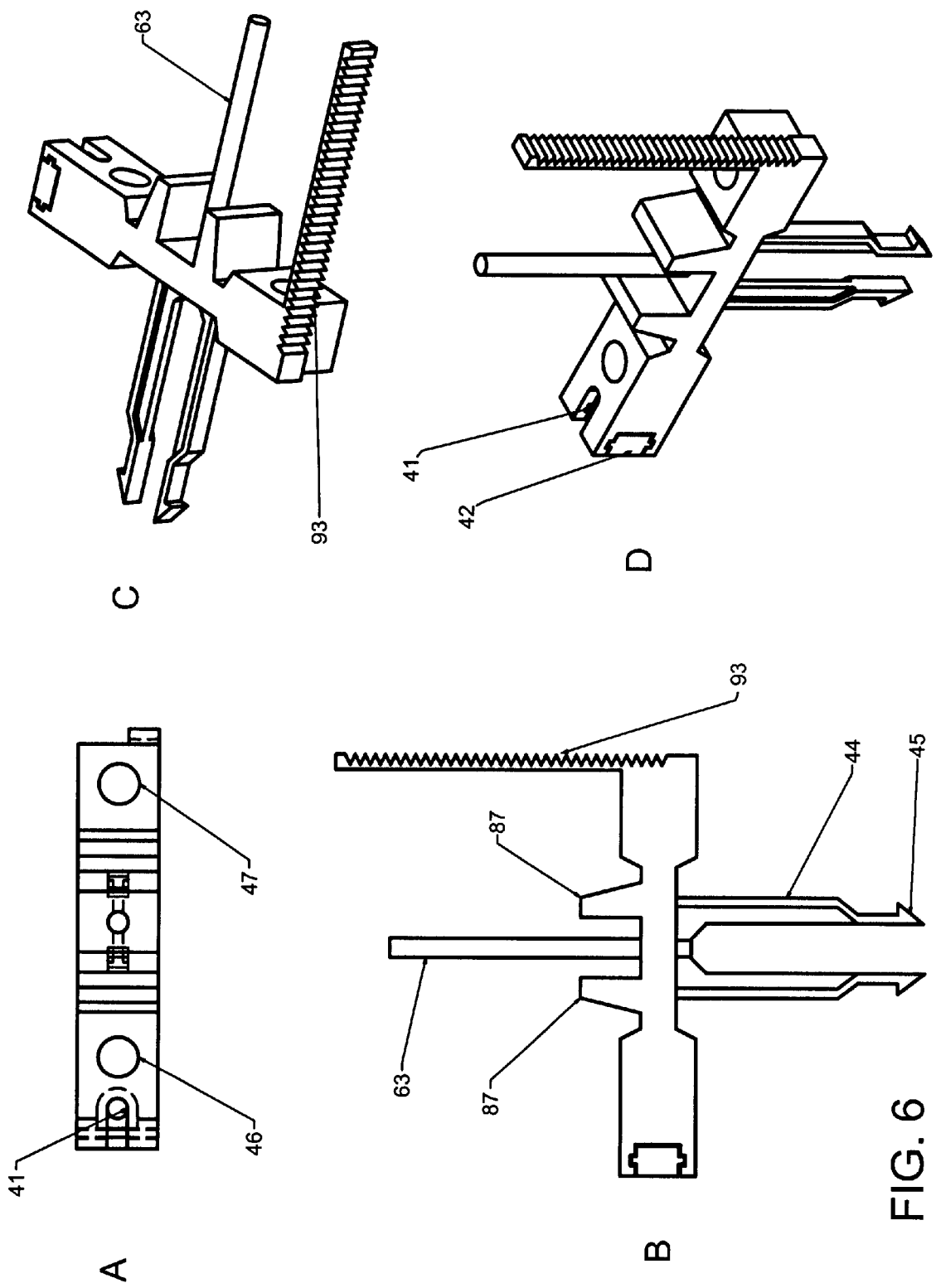
FIG. 6 shows several isometric and two-dimensional views of the cannula slide.

FIG. 6 further depicts various aspects of the cannula slide from several perspectives. FIG. 6A is a front view, FIG. 6B is a top view, and FIGS. 6C and 6D are two isometric views of the cannula slide.

Figure 7:
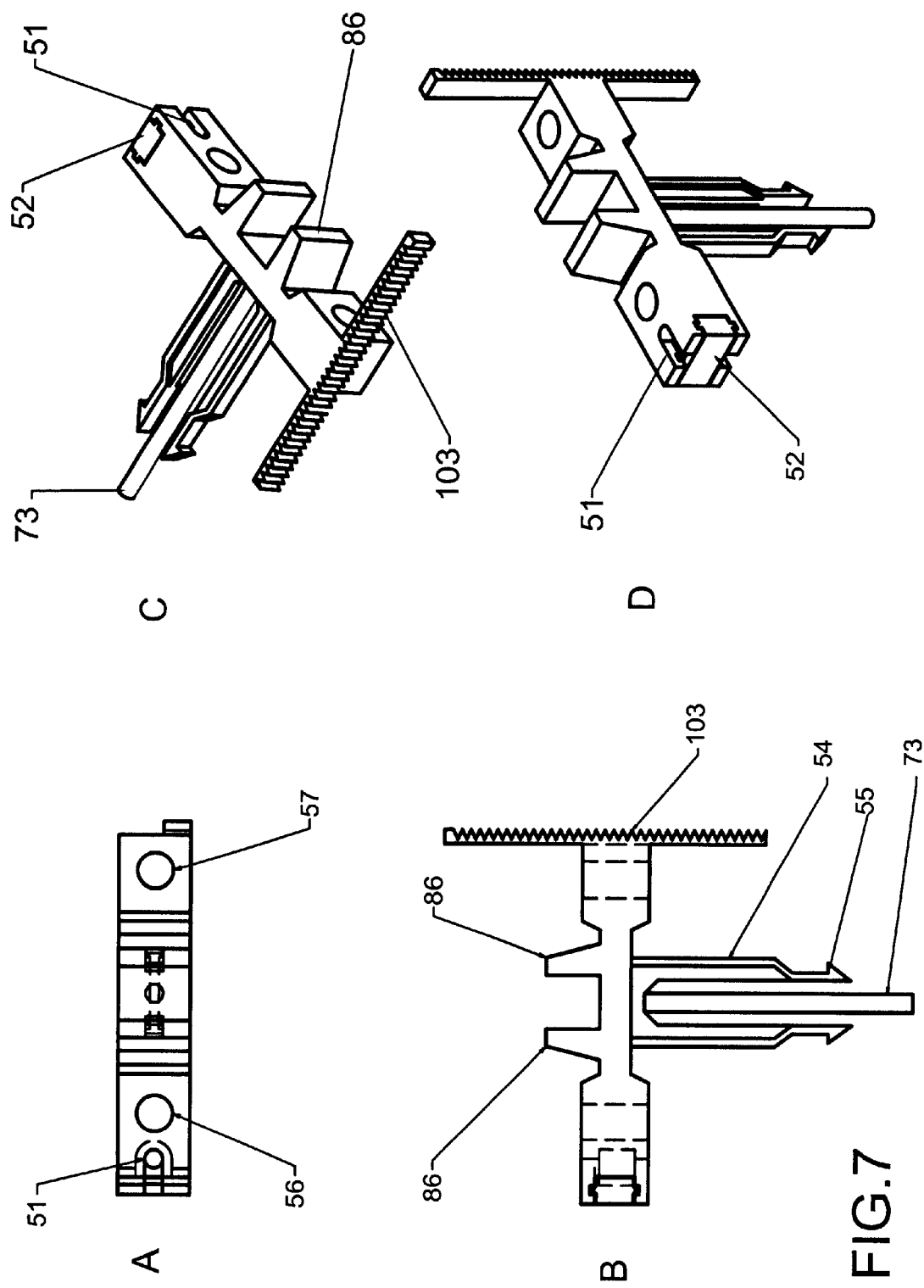
FIG. 7 shows several isometric and two-dimensional views of the stylet slide.

FIG. 7 further depicts various aspects of the stylet slide from several perspectives. FIG. 7A is a front view, FIG. 7B is a top view, and FIGS. 7C and 7D are two isometric views of the stylet slide.

The biopsy actuator also includes a cocking mechanism for retracting and retaining the cannula slide 40 against the force of compressed spring 43 and for retracting and retaining the stylet slide 50 against the force of compressed spring 53. As shown in FIGS. 3, 4 and 5 the cocking mechanism includes an electromotor 100 and its gear boxes that retract the cannula slide 40 by a mechanical drive provided through a rack 103 and pinion 102 transmission drive 101. Another electromotor 90 and its gear boxes retract the stylet slide 50 by a mechanical drive provided through a rack 93 and pinion 92 transmission drive 91. Rotating of the cannula pinion 102 induced by its electromotor results in backward (left) movement of the gear rack 103 and attached cannula slide 40 against the bias of spring 43 to cock the cannula slide 40. The cocking mechanism also includes two cannula retaining arms 44 for retaining the cannula slide 40 in a cocked position against compressed spring 43. The cannula retaining arms 44 have hooked ends 45 which hook over the middle fixed jaw 33 of the biopsy actuator base-frame to retain the cannula slide 40 in a cocked position.

Figure 8:
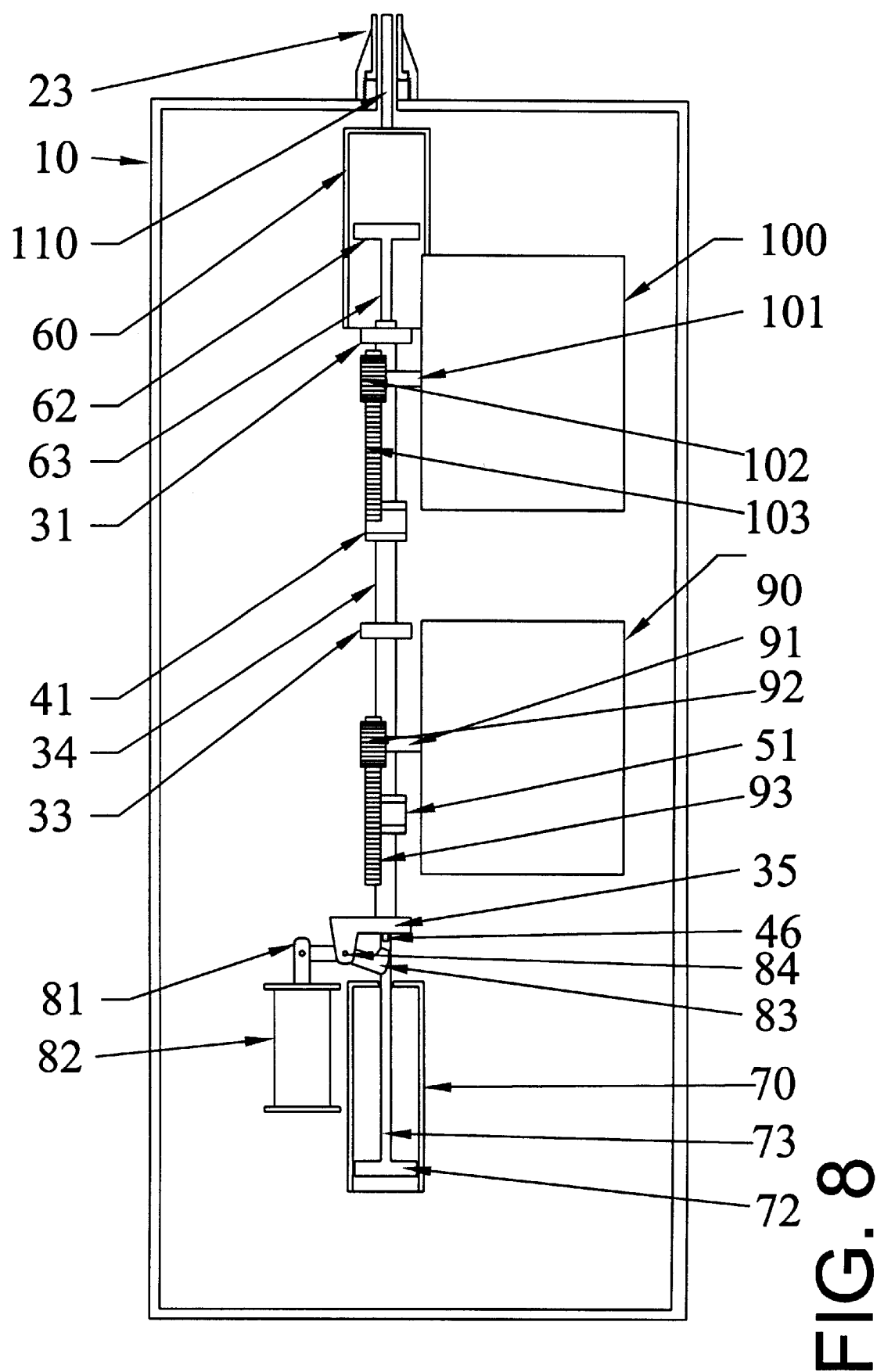
FIG. 8 is a cut-away of the biopsy actuator assembly inside the housing, viewed from front.
Figure 9:
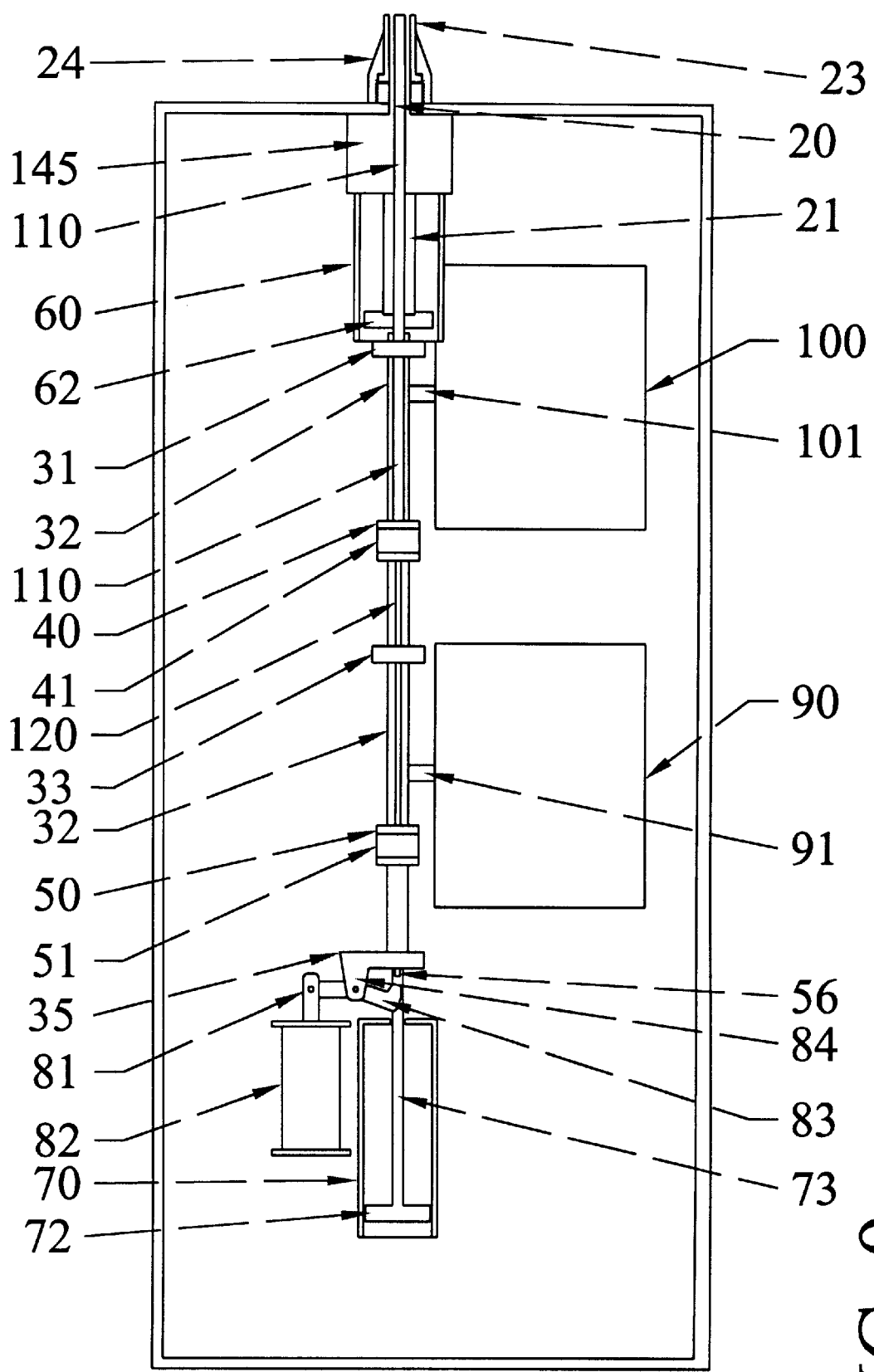
FIG. 9 is a cut-away of the biopsy actuator assembly inside the housing, viewed from back.

Rotating of the stylet pinion 92 induced by its electromotor results in backward (left) movement of the gear rack 93 and attached stylet slide 50 against the bias of the stylet spring 53 to cock the stylet slide 50. The cocking mechanism also includes two stylet retaining arms 54 for retaining the stylet slide 50 in a cocked position against compressed spring 53. The stylet retaining arms 54 have hooked ends 55 which hooks over the left fixed jaw 35 of the biopsy actuator base frame to retain the stylet slide 50 in a cocked position The biopsy actuator also includes a firing mechanism for firing the biopsy actuator to release the cannula slide 40 and the stylet slide 50 from their cocked positions, thereby propelling a stylet wire 120 and the cannula flexible hollow shaft 110. This movement results in propelling of the stylet needle 129 and the cannula needle 119 of the biopsy needle assembly to take a biopsy sample of tissue in a patient's body. Referring to FIG. 1, the firing mechanism includes a releasing activator button 13 and a firing button 14 on the front panel of the housing 10. In addition, a pedal firing button 19 is a counter part of firing button 14 on the housing 10. Pushing of the releasing activator button 13 permits the biopsy actuator to be fired whithin 20 second by pushing of the firing button 14 or its counterpart pedal firing button 19. Pushing of the electrical firing button 14 during the permited interval results in the activation of the releasing assembly 80. FIGS. 8 & 9 are a cut-away of the biopsy actuator assembly veiwed from front and back. These figures with an isometric view provided in FIG. 5 better show the releasing assembly 80. Activation of the releasing assembly 80 results in retraction of the core shaft 81 into the electromagnet coil 82 due to magnetic field strength. The core shaft 81 is joined to the releasing lever 83 on its end and its movement results in pivot of the releasing lever 83 on its middle axis pin 84 that is situated on the left fixed jaw 35 of the base frame. This pivot movement causes the other end of the releasing lever 83 to move toward the hooked end 55 of the retaining arms 54 of the stylet slide 50. Pushing on the hooked end 55 of the stylet retaining arms 54 causes the hooked ends 55 of the retaining arms 54 to move toward each other and lift from the left fixed jaw 35 and release the stylet slide 50 from a cocked position and allows spring 53 to expand, thereby propelling the stylet slide 50 to a forward position. The projections 86 on the stylet slide 50 eventually strike the hooked ends 45 of the cannula retaining arms 44, causing the hooked ends 45 to lift, thereby releasing the cannula slide 40 from a cocked position and allowing spring 43 to expand, thereby propelling the cannula slide 40 forward (right) in phased sequence.

The biopsy actuator 30 also includes a safety mechanism for preventing the accidental firing of the biopsy actuator 30. Referring to FIG. 1, the safety mechanism includes an electronic timer based electrical switch 13 on the front panel of the housing. Inadvertent pushing of the firing button 14 on the front panel of the housing or pedal firing button 19 will not result in actuating of the biopsy actuator. Pushing of these buttons can only fire the actuator in permitted period that starts just after pushing of the releasing activator button 13.

Figure 10:
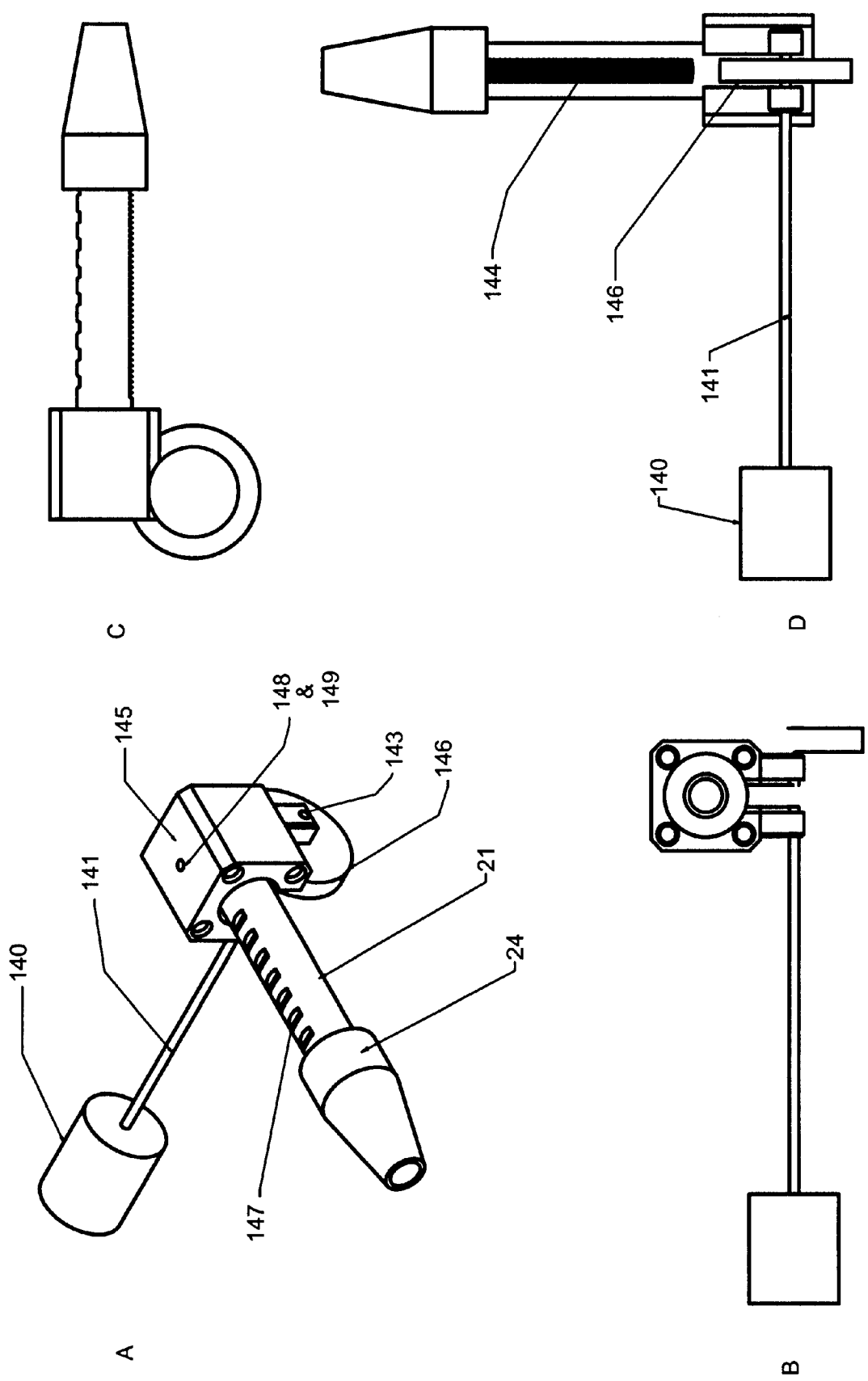
FIG. 10 shows several isometric and two-dimensional views of the assembly that control the depth of invasion of the biopsy needles inside the biopsied organ.

One embodiment of the invention is directed to the problem of depth of invasion of the needle biopsy. As depicted in FIG. 1, the invention provides a control knob 140 the can change the position of the guide tube 23 in respect to the housing 10. Because the length of movement of the stylet slide 50 and the cannula slide 40 can not be changed easily, the length of movement of the stylet needle 129 and the cannula needle 119 are constant. However if we change the position of the guide tube 23 in proportion to the housing 10, the length of protrusion of the tip the stylet 128 and the cannula 118 from tip of the guide tube 29 (depth of the invasion of the needles) could be determined precisely. Refer to FIG. 2, Extending the cannula flexible hollow shaft 110 and the stylet wire from their hubs 111 & 121 through an opening 20 on the right wall of the housing 10, they pass through a hollow shaft 21 that is coupled to the proximal end of the guide tube 23 by the guide tube nut 24. The hollow shaft 21 that is coupled to the proximal end of the guide tube 23 on its end, slides within a bush 145 that is fixed to the right wall of the housing 10. As it is shown in FIG. 10 the linear movement of the hollow shaft 21 inside the bush 145 is provided by a rack and pinion 144 & 146 transmission drive. The underneath aspect of the hollow shaft is shaped in to a rack gear 144 which will be engaged with a pinion 146 that could be turned by turning of the biopsy depth control knob 140. The biopsy depth control knob 140 connected to the pinion 146 through a joining arm 141. The pinion rotates on its axis 143, between two projections provided on the bush 145 and this results in the linear movement of the rack gear 144 on the hollow shaft 21. The adjustment of the depth of the biopsy specimen is controled within five milimeter percision by a ball and socket 147 & 148 mechanism that is supplied on the upper portion of the bush 145. This mechanism can make several stops in the journey of the hollow shaft inside of the bush. The distance between each stop is 5 milimeters. The stops are made available by engagement of the grooves 147 on the upper aspect of the hollow shaft 21 to a ball 148 that is pushed in to the grooves by a small coiled spring 149. These stops not only adjust the depth of the tissue needle invasion precisely, but also prevent unintentional guide tube movement during taking the biopsy specimen. When the biopsy specimen is going to be obtained through a percutaneous route, the piercing tip of the stylet 128 could be protruded slightly from tip of the guide tube 23 by adjusting the biopsy depth control knob 140, for better penetration of the subcutaneous and other intervenening tissue before firing the biopsy actuator. This is not necessary in endoscopic or laparasopic routes of the biopsy procedure.

Yet another embodiment of the present invention addresses the need to control the forward movement speed of the stylet and the cannula. Referring to FIG. 3 the apparatus comprises a 2 speed control cylinder that can control the speed of the movement of the cannula and the stylet slides. The cannula speed control cylinder 60 is seen at the right side of the biopsy actuator 30. It contains a piston 62 that moves within the cylinder 60 by its connection to the cannula slide 40 through a joining arm 63. The cylinder includes an outlet 61 that permits exit of the compressed air during the movement of the piston 62. This outlet is connected via a hosepipe 64 to a regulator valve 65 that can be adjusted by a control knob 16 on the front panel of the housing 10. The stylet speed control cylinder 70 is seen at the left side of the biopsy actuator 30. It contains a piston 72 that moves within the cylinder 70 by its connection to the stylet slide 50 through a joining arm 73. The cylinder includes an outlet 71 that permits exit of the compressed air during the movement of the piston 72. This outlet is connected via a hosepipe 74 to the regulator valve 75 that can be adjusted by a control knob 16 on the front panel of the housing 10.

Another aspect of the present invention involves the automated withdrawal of the biopsy needles from the sampled tissue. This withdrawal is performed while the biopsy actuator is being cocked by the electromotors 90 & 100 drive. Initiation of this withdrawal movement is started after a lag time that permits the appliance of the electrocautery current. This lag time would be started just after severing and collecting of the tissue by the cannula needle 129 and would be terminated just before initiation of the needle withdrawal. The electrocautery current is applied to the cannula hub 111 at the initiation of the lag time by a micro switch that is activated only when the cannula slide projections 87 strikes the right fixed jaw 31 of the biopsy actuator 30 base-frame.

Further aspects of the present invention deal with a mechanism for sampled tissue collection after the biopsy taking. This mechanism is triggered by a specimen retrieval button 15 on the front panel of the housing 10. This mechanism also includes a safety mechanism for preventing the accidental release of the retrieval button 15. The safety mechanism includes an electronic timer based electrical switch on the front panel of the housing. Pushing of the retrieval button 15 can only release the stylet slide for tissue retrieval in a permited period (20 seconds) that starts just after pushing of the releasing activator button 13. Pushing of the retrieval button 15 in the permitted period that would be announced by a beeper, results in activation of the releasing assembly 80. Activation of the releasing assembly 80 results in retraction of the core shaft 81 into the electromagnet coil 82 and finally results in release of the stylet slide 50 from a cocked position and allows spring 53 to expand, thereby propelling the stylet slide 50 to a forward position just similar to the usual biopsy taking procedure initial stage. The great difference between the tissue retrieval process and the firing process resides in the forward movement speed of the stylet slide. As mentioned above, the stylet forward speed controlling assembly is composed of a piston 72 and a cylinder 70 with an outlet 71. As it is shown in FIG. 11, the outlet 71 is connected via a hosepipe 74 to the regulator valve 75 that is controled by a control knob 16 on the front panel of the housing 10. The connecting hosepipe 74 passes through a passageway 76 that can be regulated by the specimen retrieval button 15. The compressed air might pass through this passageway without any significant resistance only if the button is not pushed. Pushing of the specimen retrieval button decreases the opening diameter of passageway 76 to such an amount that compressed air might pass with significant resistance, therefore decreasing the forward movement speed of the stylet slide 50 significantly. Slow movement of the stylet slide 50 produces a touch rather than a stroke of the stylet slide projection 86 to the hooked end of the cannula retaining arms 45 and this force would be inadequate to release the cannula slide 40 from its cocked position. The result is a smooth protrusion of the stylet needle from the tip of the cannula and guide tube without release of the cannula needle. This allows the physician to collect the biopsied tissue from the stylet needle slot 127. Releasing of the specimen retrieval button results in activation of the stylet cocking mechanism and backward movement of the stylet slide 50 and the stylet needle 129 to its cocked position.

The electrocautery current will be provided from an external electrocautery device that is connected to the housing through a cable 131. Viewing the FIG. 1 the current can be switched on/off by the electrocautery main switch 130 on the front panel of the housing 10. This switch 130 permits taking a biopsy with or without electrocautery appliance. An electrical wire connect the electrocautery current from the main switch 130 to a microswitch that is positioned on the right fixed jaw 31 of the base-frame and another electrical wire connect the electrocautery current from the microswitch to an electrode in the cannula slide recess 41. This electrode is in contact with the cannula hub 111. Triggering of the microswitch by the cannula slide 40 on termination of its journey on the guideway shafts results in appliance of the electrocautery current to the cannula hub 111 and then to the cannula flexible hollow shaft 110. This shaft transmits the current to the cannula needle 119 while it is inside the biopsied tissue. The current will pass from the surface of the cannula needle 119 to the surrounding tissue and coagulate the vessels in the biopsy track. Due to good electrical conductivity of the cannula needle 119, the current will not pass through the biopsied tissue inside the cannula needle. On the other hand, the cannula has conductivity sufficiently high to remove heat from the cannula needle to prevent thermal damage of the tissue inside of the cannula while delivering power to the surrounding tissue to produce coagulation.

Although the type and magnitude of the electrocautery current can be determined by changing the setting of the elecrocautery device, another embodiment of the present invention makes it possible to control the duration of electrocoagulation time by adjusting the time interval between termination of the tissue cutting and collecting by the cannula needle 119 and initiation of needle withdrawal. The lag time is controlled by an electronic timer regulated by a control knob 17 on the front panel of the housing 10. Changing the duration of the lag time, a physician would be able to control the duration of contact of the cannula to the surrounding tissue and therefore determine the degree of electrocoagulation that is necessary for special circumstances.

C—Biopsy needle assembly: A biopsy needle assembly is used with the biopsy actuator 30 for taking a biopsy sample of the tissue of interest. FIG. 12 shows the biopsy needle assembly apart from biopsy actuator 30. At one end of the biopsy needle assembly, there are needle sampling tips for insertion into the patient's body to obtain the tissue sample. These are the cannula cuting tip 118 and the stylet piercing tip 218. At the other end are needle hubs 111 and 121 which engage the needle assembly with the biopsy actuator 30. The cannula hub 111 is made of metal and securely attached to the cannula flexible hollow shaft 110. It is disposed in a recess 41 in the stylet slide 40. Further shown in FIG. 13, the cannula hub has a middle groove 112 between two shoulders 113 & 114 that mates a collar in the cannula recess 41 in the cannula slide to secure the hub 111 inside the recess 41. In addition the asymetric shape of the cannula hub 111 will not allow the hub to rotate within the recess. The cannula hub 111 can be disengaged from the cannula slide 40 easily by opening of the cannula slide cap 42 and removing of the cannula hub 111 from the cannula slide recess 41. The stylet hub 121 is securely attached to the stylet wire 120 and disposed in a recess 51 in to the stylet slide 50. FIG. 14 shows the stylet hub has a middle groove 122 between two shoulders 123 & 124 that mates a collar in the stylet recess 51 in the stylet slide 50 to secure the hub 121 inside the recess 51. In addition the asymetric shape of the stylet hub 121 will not allow the hub to rotate within the recess 51.The stylet hub 121 can also be disengaged from the stylet slide easily by openning of the stylet slide cap 52 and removing of the stylet hub 121 from the the stylet slide recess 51.

The cannula flexible hollow shaft 110 is a flexible hollow tube preferably formed of coiled stainless steel wire. It is attached securely to the cannula hub 111 on its proximal end and coupled to the cannula needle 119 at the distal end. Upon assembly, the cannula needle 119 and the cannula flexible hollow shaft 110 is inserted through guide tube 23 and is extendable therefrom. When firing the biopsy actuator, the cannula flexible hollow shaft 110 transmits the linear movement of the cannula slide 40 from the cannula hub 111, at its proximal end to the cannula needle 119 at its distal end.

The stylet wire 120 is a flexible stainless steel wire that is disposed within the cannula flexible hollow shaft 110 and telescopes with respect thereto. The proximal end of the stylet wire couples securely to the stylet hub 121 while its distal end is attached to the proximal end of the stylet needle 129. Upon firing of the biopsy actuator, the stylet wire 120 transmits the linear movement of the stylet slide 50 from the stylet hub 121, at its proximal end to the stylet needle 129 at its distal end.

FIG. 15 shows a two dimensional views of the tip of the biopsy needles, which can be used to take a biopsy sample. The biopsy needles include the cannula needle 119 and the stylet needle 129. As FIG. 15B shows, the cannula needle 119 is a hollow needle that is disposed inside of the guide tube 23. Its distal end has a circular cutting tip 118, which is inserted into the patient's body during tissue sampling while its proximal end is permanently coupled to the cannula flexible hollow shaft 110 and remains outside of the patient's body.

As FIG. 15A shows, the stylet needle 129 is a solid needle that is disposed inside of the cannula needle 119. It has a piercing tip 128 on its distal end for piercing tissue inside of a patient's body during the taking of a biopsy sample. The stylet needle proximal end is coupled permanently to the stylet wire 120 and remains outside of the patient's body. The stylet needle 129 also has a tissue-sampling slot 127 in which a biopsy tissue sample can be collected.

FIG. 16 shows isometric views of the tip of the biopsy needle assembly, which can be used to take a biopsy sample. The biopsy needle assembly is comprised of biopsy needles and the guide tube 23. The guide tube 23 is a hollow flexible plastic tube that covers the cannula flexible hollow shaft 110, the cannula needle 119, the stylet wire 120 and the stylet needle 129. The guide tube 23 is held in the physician's hand and can be used to direct the biopsy needle assembly toward the desired direction. It remains outside of the patient's body during the taking of the biopsy sample. Although the cannula needle 119 and the stylet needle 129 are substantially straight and rigid, the cannula flexible hollow shaft 110, the stylet wire 120 and guide tube 23 are all made up of flexible material to enable the physician to easily manipulate the direction of the biopsy needle assembly probe.

Referring to FIGS. 15C & 16A, the piercing tip 128 of the stylet needle 129 of the biopsy needle assembly is initially in a retracted position substantially within the hollow interior of the guide tube 23. Upon firing the biopsy actuator 30 (FIGS. 15D & 16C), the stylet wire 120 is moved relative to the cannula flexible hollow shaft 110 and the guide tube, such that the stylet needle 129 and its piercing tip 128 protrudes from the cannula needle 119 and guide tube end 29 to pierce the tissue of interest with piercing tip 128 and to fill tissue sampling slot 127 with the tissue to be sampled. The cannula flexible hollow shaft 110 is then moved relative to the stylet wire and guide tube (FIGS. 15E & 16D) thereby moving the cannula needle 119 and its cutting tip 118, down over the tissue sample, which filled the tissue sampling notch 127 of the stylet needle 129, thereby severing the tissue sample from the patient's body and holding the severed sample in the tissue sampling notch 127 which ends up substantially completely within the cannula needle 119 (FIGS. 15F & 16E). After severing the tissue with the cutting end 118 of the cannula, the electrocautery current is applied to the surrounding tissue through the cannula metal surface while the needle is within the biopsy track.

By adjusting the depth of the needle invasion control knob 140 on the front panel of the housing 10, the physician is able to protrude slightly the piercing tip 128 of the stylet needle 129 from the distal end 29 of the guide tube 23 for performing a biopsy via percutaneous route. (FIG. 16B) This is done for better penetration of the subcutaneous and other intervening tissue and is not necessary in endoscopic or laparasopic biopsy procedures. After penetration of the subcutaneous and other intervening tissue by the piercing tip 128 of the stylet needle 129, the depth of needle invasion control knob 140 could be adjusted to the desired value before firing the biopsy actuator 30.

In order to collect the biopsied tissue, the stylet needle 129 will be protruded slowly from the cannula needle 119 and the guide tube 23 by pushing of the tissue retreival button 15 on the front panel of the housing and the collected tissue sample can be recovered for analysis.

Although the needle assembly of the present invention may be sterilized for reuse, an advantage of the simple structure needle assembly is that it can be made relatively inexpensively and can, therefore, be economically disposed of after a single use, thereby avoiding the cost and complexity of sterilization for reuse.

The foregoing description of the invention has been presented for purposes of illustration and description. Further, the description is not intended to limit the variations and modifications commensurate with the above teachings, and the skill or knowledge in the relevant art are within the scope of the present invention. The preferred embodiment described herein above is further intended to explain the best mode known of practicing the invention and to enable others skilled in the art to utilize the invention in various embodiments and with the various modifications required by their particular applications or uses of the invention.

Having described the specification for the new Automated Hot Needle Biopsy and Device, I submit the following as my claims:

1. A biopsy device for taking a core biopsy from internal organs, the biopsy device comprising:

a biopsy needle assembly, said biopsy needle assembly comprising:

a flexible plastic guide tube having a proximal end extending from a housing, a distal end terminating away from said housing, and a longitudinal axis extending between said proximal and distal guide tube ends;

a substantially straight, cylindrical cannula needle having a sharpened annular distal end for cutting tissue and a proximal end terminating in a cannula hub, said cannula needle being moveably disposed within said guide tube such that said sharpened distal end of said cannula needle is extendable from said distal end of said guide tube; and a substantially straight stylet needle having a sharpened distal end for puncturing tissue, a proximal end terminating in a stylet hub, and a tissue sample receiving slot located adjacent to said distal end, said stylet needle being moveably disposed within said cannula needle such that said sharpened distal end of said stylet needle is extendable from said distal end of said cannula needle; and a table-top biopsy instrument actuating device adapted to be positioned on a bedside table adjacent to a patient for actuating said biopsy needle assembly, said table-top biopsy instrument actuating device comprising:

a housing having a front panel including:
  a plurality of controlling switches and knobs including at least a main power switch, a cautery main switch, a releasing activator button, a firing button, a specimen retrieval button, a stylet and cannula forward speed control knob, a withdrawal lag time control knob, and a depth of needle invasion control knob; and
  a digital display for indicating information regarding position and energized status of said biopsy instrument actuating device such that a user can be visually informed of a status of the biopsy device; and
a biopsy actuator disposed within the housing, the biopsy actuator comprising:
  a cannula slide having a recess for securely engaging said cannula hub to transfer linear movement of said cannula slide to said cannula needle;
  a stylet slide having a recess for securely engaging said stylet hub to transfer linear movement of said stylet slide to said stylet needle;
  a base-frame including two parallel, solid cylindrical shafts forming a sliding guide-way for movement of the cannula slide and the stylet slide, said base-frame shafts being kept parallel by three fixed jaws;
  a stylet spring mechanism for acting on said stylet slide to move said distal end of the stylet needle away from said housing, wherein said stylet spring mechanism is placed into an energized mode to store energy and is then released from said energized mode to propel said stylet slide along said base-frame shafts, such that said distal end of said stylet needle is extended from said distal end of said cannula needle to capture a tissue sample within said tissue sample receiving slot;
  a cannula spring mechanism for acting on said cannula slide to move said distal end of the cannula needle away from said housing, wherein said cannula spring mechanism is placed into an energized mode to store energy and is then released from said energized mode to propel said cannula slide along said base-frame shafts, such that said distal end of said cannula needle is extended from said distal end of said guide tube to enclose said tissue sample receiving slot of said stylet needle, thereby severing a tissue sample disposed within said tissue sample receiving slot;
  a stylet latch mechanism selectively releasable by an electromagnetic releasing assembly for releasably holding said stylet spring mechanism in said energized mode; said stylet latch mechanism being releasable in response to striking of a releasing lever to hook ends of retaining arms of said stylet slide;
  a cannula latch mechanism for releasably holding said cannula spring mechanism in said energized mode, said cannula latch mechanism being releasable subsequent to release of said stylet spring mechanism by striking of said stylet slide to hook ends of retaining arms of said cannula slide.

2. The biopsy device of claim 1 wherein said stylet needle and said cannula needle are slidable with respect to each other between a position in which said cannula needle covers said tissue sample receiving slot of said stylet needle and a position in which said tissue sample receiving slot in said stylet needle is exposed beyond said distal end of said cannula needle for receiving a tissue specimen.

3. The biopsy device of claim 1 wherein said biopsy needle assembly is disposable.

4. The biopsy device of claim 1 wherein said biopsy actuator further comprises:
  a cocking mechanism for retracting and retaining said cannula slide against the force of compressed cannula springs and for retracting and retaining said stylet slide against the force of compressed stylet springs, said cocking mechanism comprising:
    two electro motors for retracting said cannula slide and said stylet slide through a mechanical drive produced by rack and pinion transmission drive; and
    two retaining arms on each slide for retaining said slides in a cocked position against the compressed springs, said retaining arms having hooked ends which hook over said fixed jaws of said biopsy actuator base-frame to retain said slides in a cocked position.

5. The biopsy device of claim 4 wherein said biopsy actuator further comprises:
  a firing mechanism for releasing said cannula slide and said stylet slide from cocked positions, said firing mechanism comprising:
    said releasing activator button and said firing button on the front panel of said housing;
    a pedal firing button as a counter part of said firing button on the front panel of said housing;
    a releasing electromagnet; and
    a releasing lever,
    wherein said firing mechanism operates by sequential pushing of said releasing activator button and said firing button that results in activation of the releasing electromagnet which moves said releasing lever, wherein pivoting of said releasing lever results in striking the stylet latch mechanism, pushing the hooked ends of said stylet retaining arms toward each other to lift the hooked ends from said fixed jaw, thereby releasing said stylet slide from the cocked position and allowing said stylet springs to expand to propel said stylet slide to a forward position, wherein projections on the stylet slide strike said cannula latch mechanism, pushing said hooked ends of said cannula retaining arms, causing said hooked ends to lift, thereby releasing said cannula slide from a cocked position and allowing said cannula springs to expand to propel said cannula slide forward in phased sequence.

6. The biopsy device of claim 4 wherein said biopsy actuator further comprises:
  a safety mechanism for preventing accidental firing of the biopsy actuator, said safety mechanism including an electronic timer based electrical switch on the front panel of the housing, wherein pushing of said releasing activator button permits the biopsy to be performed by pressing said firing button within a 20 second window that is announced by a beeper.

7. The biopsy device of claim 4 wherein said biopsy actuator further comprises:
  means for controlling forward movement speed of said stylet slide including a stylet cylinder and a stylet piston slidably disposed within said stylet cylinder, wherein said stylet piston connects to said stylet slide through a stylet connecting arm, and wherein said means for controlling forward movement speed of said stylet slide operates by compressing air inside said stylet cylinder by movement of said stylet piston such that air exiting from a small outlet at an end of said stylet cylinder is controlled by a regulating valve operated by said forward speed control knob on the front panel of said housing; and means for controlling the forward movement speed of said cannula slide including a cannula cylinder and a cannula piston disposed within said cannula cylinder; wherein said cannula piston connects to said cannula slide through a cannula connecting arm, and wherein said means for controlling the forward movement speed of said cannula slide operates by compressing air inside said cannula cylinder by movement of said cannula piston such that air exiting from a small outlet at an end of said cannula cylinder is controlled by a regulating valve operated by said forward speed control knob on the front panel of said housing.

8. The biopsy device of claim 4 wherein said biopsy actuator further comprises:

means for applying an electrocautery current after taking a biopsy specimen by connecting said cannula needle to a monopolar electrocautery device after severing tissue by forward movement of said cannula needle over said stylet needle in the tissue, wherein an extent of electro coagulation is determined by adjusting the magnitude of the electrocautery current and the withdrawal lag time that said cannula needle remains in the tissue after taking the biopsy specimen and before withdrawal.

9. The biopsy device of claim 4 wherein said biopsy actuator further comprises:

a biopsy tissue retrieval mechanism including said specimen retrieval button on said front panel of said housing, wherein pushing said specimen retrieval button results in slow release of said stylet slide without releasing said cannula slide, thereby permitting protrusion of said stylet needle such that said tissue sample receiving slot is exposed for collecting of the biopsied tissue; and means for controlling forward movement speed of said stylet slide during retrieval of the biopsied tissue including a stylet cylinder and a stylet piston disposed within said stylet cylinder, wherein said means for controlling forward movement speed of said stylet slide operates by compressing air inside said stylet cylinder by movement of said stylet piston, and wherein air exiting from a small outlet at an end of said stylet cylinder is controlled by a regulating valve activated by pushing said specimen retrieval button on said front panel of said housing.

* * * * *